US012773262B2

(12) United States Patent
Gutbrod et al.

(10) Patent No.: US 12,773,262 B2
(45) Date of Patent: Oct. 27, 2026

(54) OVERLAY OF DYNAMIC SPATIAL DATA ON USER INTERFACE FOR ABLATION BY IRREVERSIBLE ELECTROPORATION

(71) Applicant: Boston Scientific Scimed, Inc., Maple Grove, MN (US)

(72) Inventors: Sarah Renee Gutbrod, Medford, MA (US); Brendan Early Koop, Ham Lake, MN (US); Andrew L. De Kock, Ham Lake, MN (US); Allan Charles Shuros, St Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 413 days.

(21) Appl. No.: 17/320,790

(22) Filed: May 14, 2021

(65) Prior Publication Data

US 2021/0369341 A1 Dec. 2, 2021

Related U.S. Application Data

(60) Provisional application No. 63/030,042, filed on May 26, 2020.

(51) Int. Cl.

*A61B 18/14* (2006.01)
*A61B 90/00* (2016.01)

(Continued)

(52) U.S. Cl.

CPC .......... *A61B 18/1492* (2013.01); *A61B 90/37* (2016.02); *A61N 1/327* (2013.01);

(Continued)

(58) Field of Classification Search

CPC ................ A61B 18/1492; A61B 90/37; A61B 2018/00267; A61B 2018/00357;

(Continued)

(56) References Cited

U.S. PATENT DOCUMENTS

| | | | |
|---|---|---|---|
| 4,200,104 | A | 4/1980 | Harris |
| 4,470,407 | A | 9/1984 | Hussein |

(Continued)

FOREIGN PATENT DOCUMENTS

| | | | |
|---|---|---|---|
| AU | 741167 | B2 | 11/2001 |
| EP | 1042990 | A1 | 10/2000 |

(Continued)

OTHER PUBLICATIONS

Du Pre, B.C. et al., "Minimal coronary artery damage by myocardial electroporation ablation," Europace, 15(1):144-149 (2013).

(Continued)

*Primary Examiner* — Beverly M Flanagan
*Assistant Examiner* — Abigail M Ziegler
(74) *Attorney, Agent, or Firm* — Nelson Mullins Riley & Scarborough LLP

(57) ABSTRACT

A system for ablation by electroporation including a catheter having electrodes, a display, and a controller. The controller is to generate, based on models of electric fields, graphical representations of the electric fields that can be produced using the electrodes, and overlay, on the display, the graphical representations of the electric fields and an anatomical map of a patient to aid in planning the ablation by electroporation, prior to delivering energy.

16 Claims, 9 Drawing Sheets

(51) Int. Cl.
*A61N 1/32* (2006.01)
*A61B 18/00* (2006.01)

(52) U.S. Cl.
CPC ............... *A61B 2018/00267* (2013.01); *A61B 2018/00357* (2013.01); *A61B 2018/00577* (2013.01); *A61B 2018/00613* (2013.01); *A61B 2018/00702* (2013.01); *A61B 2018/00875* (2013.01); *A61B 2018/1467* (2013.01)

(58) Field of Classification Search
CPC .......... A61B 2018/00577; A61B 2018/00613; A61B 2018/00702; A61B 2018/00875; A61B 2018/1467; A61B 2034/104; A61B 34/10; A61N 1/327
See application file for complete search history.

(56) References Cited

U.S. PATENT DOCUMENTS 4,739,759 A 4/1988 Rexroth et al.
5,234,004 A 8/1993 Hascoet et al.
5,242,441 A 9/1993 Avitall
5,257,635 A 11/1993 Langberg
5,281,213 A 1/1994 Milder et al.
5,304,214 A 4/1994 Deford et al.
5,306,296 A 4/1994 Wright et al.
5,334,183 A 8/1994 Wuchinich
5,334,193 A 8/1994 Nardella
5,341,807 A 8/1994 Nardella
5,342,301 A 8/1994 Saab
5,398,683 A 3/1995 Edwards et al.
5,443,463 A 8/1995 Stern et al.
5,454,370 A 10/1995 Avitall
5,515,848 A 5/1996 Corbett et al.
5,531,685 A 7/1996 Hemmer et al.
5,545,161 A 8/1996 Imran
5,578,040 A 11/1996 Smith
5,617,854 A 4/1997 Munsif
5,624,430 A 4/1997 Eton et al.
5,667,491 A 9/1997 Pliquett et al.
5,672,170 A 9/1997 Cho et al.
5,700,243 A 12/1997 Narciso, Jr.
5,702,438 A 12/1997 Avitall
5,706,823 A 1/1998 Wodlinger
5,722,400 A 3/1998 Ockuly et al.
5,722,402 A 3/1998 Swanson et al.
5,749,914 A 5/1998 Janssen
5,779,699 A 7/1998 Lipson
5,788,692 A 8/1998 Campbell et al.
5,810,762 A 9/1998 Hofmann
5,833,710 A 11/1998 Jacobson
5,836,874 A 11/1998 Swanson et al.
5,836,942 A 11/1998 Netherly et al.
5,836,947 A 11/1998 Fleischman et al.
5,843,154 A 12/1998 Osypka
5,849,028 A 12/1998 Chen
5,860,974 A 1/1999 Abele
5,863,291 A 1/1999 Schaer
5,868,736 A 2/1999 Swanson et al.
5,871,523 A 2/1999 Fleischman et al.
5,876,336 A 3/1999 Swanson et al.
5,885,278 A 3/1999 Fleischman
5,895,404 A 4/1999 Ruiz
5,899,917 A 5/1999 Edwards et al.
5,904,709 A 5/1999 Arndt et al.
5,916,158 A 6/1999 Webster, Jr.
5,916,213 A 6/1999 Haissaguerre et al.
5,921,924 A 7/1999 Avitall
5,928,269 A 7/1999 Alt
5,928,270 A 7/1999 Ramsey, III
5,938,660 A 8/1999 Swartz et al.
6,002,955 A 12/1999 Willems et al.
6,006,131 A 12/1999 Cooper et al.
6,009,351 A 12/1999 Flachman
6,014,579 A 1/2000 Pomeranz et al.
6,029,671 A 2/2000 Stevens et al.
6,033,403 A 3/2000 Tu et al.
6,035,238 A 3/2000 Ingle et al.
6,045,550 A 4/2000 Simpson et al.
6,068,653 A 5/2000 LaFontaine
6,071,274 A 6/2000 Thompson et al.
6,071,281 A 6/2000 Burnside et al.
6,074,389 A 6/2000 Levine et al.
6,076,012 A 6/2000 Swanson et al.
6,090,104 A 7/2000 Webster, Jr.
6,096,036 A 8/2000 Bowe et al.
6,113,595 A 9/2000 Muntermann
6,119,041 A 9/2000 Pomeranz et al.
6,120,500 A 9/2000 Bednarek et al.
6,142,993 A 11/2000 Whayne et al.
6,146,381 A 11/2000 Bowe et al.
6,164,283 A 12/2000 Lesh
6,167,291 A 12/2000 Barajas et al.
6,171,305 B1 1/2001 Sherman
6,216,034 B1 4/2001 Hofmann et al.
6,219,582 B1 4/2001 Hofstad et al.
6,223,085 B1 4/2001 Dann et al.
6,231,518 B1 5/2001 Grabek et al.
6,245,064 B1 6/2001 Lesh et al.
6,251,107 B1 6/2001 Schaer
6,251,109 B1 6/2001 Hassett et al.
6,251,128 B1 6/2001 Knopp et al.
6,270,476 B1 8/2001 Santoianni et al.
6,272,384 B1 8/2001 Simon et al.
6,287,306 B1 9/2001 Kroll et al.
6,314,963 B1 11/2001 Vaska et al.
6,322,559 B1 11/2001 Daulton et al.
6,350,263 B1 2/2002 Wetzig et al.
6,370,412 B1 4/2002 Armoundas et al.
6,391,024 B1 5/2002 Sun et al.
6,447,505 B2 9/2002 McGovern et al.
6,464,699 B1 10/2002 Swanson
6,470,211 B1 10/2002 Ideker et al.
6,502,576 B1 1/2003 Lesh
6,503,247 B2 1/2003 Swartz et al.
6,517,534 B1 2/2003 McGovern et al.
6,527,724 B1 3/2003 Fenici
6,527,767 B2 3/2003 Wang et al.
6,592,581 B2 7/2003 Bowe
6,595,991 B2 7/2003 Toellner et al.
6,607,520 B2 8/2003 Keane
6,613,046 B1 9/2003 Jenkins et al.
6,623,480 B1 9/2003 Kuo et al.
6,638,278 B2 10/2003 Falwell et al.
6,666,863 B2 12/2003 Wentzel et al.
6,669,693 B2 12/2003 Friedman
6,702,811 B2 3/2004 Stewart et al.
6,719,756 B1 4/2004 Muntermann
6,723,092 B2 4/2004 Brown et al.
6,728,563 B2 4/2004 Rashidi
6,743,225 B2 6/2004 Sanchez et al.
6,743,226 B2 6/2004 Cosman et al.
6,743,239 B1 6/2004 Kuehn et al.
6,764,486 B2 7/2004 Natale
6,780,181 B2 8/2004 Kroll et al.
6,805,128 B1 10/2004 Pless et al.
6,807,447 B2 10/2004 Griffin, III
6,892,091 B1 5/2005 Ben-Haim et al.
6,893,438 B2 5/2005 Hall et al.
6,926,714 B1 8/2005 Sra
6,955,173 B2 10/2005 Lesh
6,960,206 B2 11/2005 Keane
6,960,207 B2 11/2005 Vanney et al.
6,972,016 B2 12/2005 Hill et al.
6,973,339 B2 12/2005 Govari
6,979,331 B2 12/2005 Hintringer et al.
6,984,232 B2 1/2006 Vanney et al.
6,985,776 B2 1/2006 Kane et al.
7,001,383 B2 2/2006 Keidar
7,041,095 B2 5/2006 Wang et al.
7,113,831 B2 9/2006 Hooven
7,171,263 B2 1/2007 Darvish et al.
7,182,725 B2 2/2007 Bonan et al.

(56) References Cited

U.S. PATENT DOCUMENTS 7,195,628 B2 3/2007 Falkenberg
7,207,988 B2 4/2007 Leckrone et al.
7,207,989 B2 4/2007 Pike et al.
7,229,402 B2 6/2007 Diaz et al.
7,229,437 B2 6/2007 Johnson et al.
7,250,049 B2 7/2007 Roop et al.
7,285,116 B2 10/2007 De et al.
7,285,119 B2 10/2007 Stewart et al.
7,326,208 B2 2/2008 Vanney et al.
7,346,379 B2 3/2008 Eng et al.
7,367,974 B2 5/2008 Haemmerich et al.
7,374,567 B2 5/2008 Heuser
7,387,629 B2 6/2008 Vanney et al.
7,387,630 B2 6/2008 Mest
7,387,636 B2 6/2008 Cohn et al.
7,416,552 B2 8/2008 Paul et al.
7,419,477 B2 9/2008 Simpson et al.
7,419,489 B2 9/2008 Vanney et al.
7,422,591 B2 9/2008 Phan
7,429,261 B2 9/2008 Kunis et al.
7,435,248 B2 10/2008 Taimisto et al.
7,513,896 B2 4/2009 Orszulak
7,527,625 B2 5/2009 Knight et al.
7,578,816 B2 8/2009 Boveja et al.
7,588,567 B2 9/2009 Boveja et al.
7,623,899 B2 11/2009 Worley et al.
7,678,108 B2 3/2010 Chrisitian et al.
7,681,579 B2 3/2010 Schwartz
7,771,421 B2 8/2010 Stewart et al.
7,805,182 B2 9/2010 Weese et al.
7,842,031 B2 11/2010 Abboud et al.
7,850,642 B2 12/2010 Moll et al.
7,850,685 B2 12/2010 Kunis et al.
7,857,808 B2 12/2010 Oral et al.
7,857,809 B2 12/2010 Drysen
7,869,865 B2 1/2011 Govari et al.
7,892,232 B2 2/2011 Boese et al.
7,896,873 B2 3/2011 Hiller et al.
7,917,211 B2 3/2011 Zacouto
7,918,819 B2 4/2011 Karmarkar et al.
7,918,850 B2 4/2011 Govari et al.
7,922,714 B2 4/2011 Stevens-Wright
7,955,827 B2 6/2011 Rubinsky et al.
8,048,067 B2 11/2011 Davalos et al.
8,048,072 B2 11/2011 Verin et al.
8,100,895 B2 1/2012 Panos et al.
8,100,900 B2 1/2012 Prinz et al.
8,108,069 B2 1/2012 Stahler et al.
8,133,220 B2 3/2012 Lee et al.
8,137,342 B2 3/2012 Crossman
8,145,289 B2 3/2012 Calabro'et al.
8,147,486 B2 4/2012 Honour et al.
8,160,690 B2 4/2012 Wilfley et al.
8,175,680 B2 5/2012 Panescu
8,182,477 B2 5/2012 Orszulak et al.
8,206,384 B2 6/2012 Falwell et al.
8,206,385 B2 6/2012 Stangenes et al.
8,216,221 B2 7/2012 Ibrahim et al.
8,221,411 B2 7/2012 Francischelli et al.
8,226,648 B2 7/2012 Paul et al.
8,228,065 B2 7/2012 Wirtz et al.
8,235,986 B2 8/2012 Kulesa et al.
8,235,988 B2 8/2012 Davis et al.
8,251,986 B2 8/2012 Chornenky et al.
8,282,631 B2 10/2012 Davalos et al.
8,287,532 B2 10/2012 Carroll et al.
8,357,152 B2 1/2013 Govari et al.
8,414,508 B2 4/2013 Thapliyal et al.
8,430,875 B2 4/2013 Ibrahim et al.
8,433,394 B2 4/2013 Harlev et al.
8,449,535 B2 5/2013 Deno et al.
8,454,589 B2 6/2013 Deno et al.
8,454,594 B2 6/2013 Demarais et al.
8,463,368 B2 6/2013 Harlev et al.
8,475,450 B2 7/2013 Govari et al.
8,478,379 B2 7/2013 Osadchy et al.
8,486,063 B2 7/2013 Werneth et al.
8,500,733 B2 8/2013 Watson
8,535,304 B2 9/2013 Sklar et al.
8,538,501 B2 9/2013 Venkatachalam et al.
8,562,588 B2 10/2013 Hobbs et al.
8,568,406 B2 10/2013 Harlev et al.
8,568,410 B2 10/2013 Vakharia et al.
8,571,635 B2 10/2013 Mcgee
8,571,647 B2 10/2013 Harlev et al.
8,579,897 B2 11/2013 Vakharia et al.
8,585,695 B2 11/2013 Shih
8,588,885 B2 11/2013 Hall et al.
8,597,288 B2 12/2013 Christian
8,608,735 B2 12/2013 Govari et al.
8,628,522 B2 1/2014 Ibrahim et al.
8,632,534 B2 1/2014 Pearson et al.
8,647,338 B2 2/2014 Chornenky et al.
8,708,952 B2 4/2014 Cohen et al.
8,734,442 B2 5/2014 Cao et al.
8,771,267 B2 7/2014 Kunis et al.
8,795,310 B2 8/2014 Fung et al.
8,808,273 B2 8/2014 Caples et al.
8,808,281 B2 8/2014 Emmons et al.
8,834,461 B2 9/2014 Werneth et al.
8,834,464 B2 9/2014 Stewart et al.
8,868,169 B2 10/2014 Narayan et al.
8,876,817 B2 11/2014 Avitall et al.
8,880,195 B2 11/2014 Azure
8,886,309 B2 11/2014 Luther et al.
8,903,488 B2 12/2014 Callas et al.
8,920,411 B2 12/2014 Gelbart et al.
8,926,589 B2 1/2015 Govari
8,932,287 B2 1/2015 Gelbart et al.
8,945,117 B2 2/2015 Bencini
8,979,841 B2 3/2015 Kunis et al.
8,986,278 B2 3/2015 Fung et al.
8,996,091 B2 3/2015 De et al.
9,002,436 B2 4/2015 Wu et al.
9,002,442 B2 4/2015 Harley et al.
9,005,189 B2 4/2015 Davalos et al.
9,005,194 B2 4/2015 Oral et al.
9,011,425 B2 4/2015 Fischer et al.
9,044,245 B2 6/2015 Condie et al.
9,055,959 B2 6/2015 Vaska et al.
9,072,518 B2 7/2015 Swanson
9,078,667 B2 7/2015 Besser et al.
9,101,374 B1 8/2015 Hoch et al.
9,113,911 B2 8/2015 Sherman
9,119,533 B2 9/2015 Ghaffari
9,119,634 B2 9/2015 Gelbart et al.
9,123,099 B2 9/2015 Hundley et al.
9,131,897 B2 9/2015 Harada et al.
9,155,590 B2 10/2015 Mathur
9,162,037 B2 10/2015 Belson et al.
9,173,611 B2 11/2015 Deno et al.
9,179,972 B2 11/2015 Olson
9,186,481 B2 11/2015 Avitall et al.
9,192,769 B2 11/2015 Donofrio et al.
9,198,733 B2 12/2015 Neal et al.
9,204,916 B2 12/2015 Lalonde
9,204,927 B2 12/2015 Afonso et al.
9,211,405 B2 12/2015 Mahapatra et al.
9,216,055 B2 12/2015 Spence et al.
9,233,248 B2 1/2016 Luther et al.
9,237,926 B2 1/2016 Nollert et al.
9,262,252 B2 2/2016 Kirkpatrick et al.
9,265,557 B2 2/2016 Sherman et al.
9,277,957 B2 3/2016 Long et al.
9,282,910 B2 3/2016 Narayan et al.
9,283,026 B2 3/2016 Paul et al.
9,289,258 B2 3/2016 Cohen
9,289,606 B2 3/2016 Paul et al.
9,295,516 B2 3/2016 Pearson et al.
9,301,801 B2 4/2016 Scheib
9,351,789 B2 5/2016 Novichenok et al.
9,375,268 B2 6/2016 Long
9,387,031 B2 7/2016 Stewart et al.
9,414,881 B2 8/2016 Callas et al.

(56) References Cited

U.S. PATENT DOCUMENTS

| | | | |
|---|---|---|---|
| 9,468,495 | B2 | 10/2016 | Kunis et al. |
| 9,474,486 | B2 | 10/2016 | Eliason et al. |
| 9,474,574 | B2 | 10/2016 | Ibrahim et al. |
| 9,480,525 | B2 | 11/2016 | Lopes et al. |
| 9,486,272 | B2 | 11/2016 | Bonyak et al. |
| 9,486,273 | B2 | 11/2016 | Lopes et al. |
| 9,492,226 | B2 | 11/2016 | Fish et al. |
| 9,492,227 | B2 | 11/2016 | Lopes et al. |
| 9,492,228 | B2 | 11/2016 | Lopes et al. |
| 9,510,888 | B2 | 12/2016 | Jean-Pierre |
| 9,517,103 | B2 | 12/2016 | Panescu et al. |
| 9,526,573 | B2 | 12/2016 | Lopes et al. |
| 9,532,831 | B2 | 1/2017 | Reinders et al. |
| 9,539,010 | B2 | 1/2017 | Gagner et al. |
| 9,554,848 | B2 | 1/2017 | Stewart et al. |
| 9,554,851 | B2 | 1/2017 | Sklar et al. |
| 9,700,368 | B2 | 7/2017 | Callas et al. |
| 9,724,170 | B2 | 8/2017 | Mickelsen |
| 9,757,182 | B2 | 9/2017 | Bustan et al. |
| 9,757,193 | B2 | 9/2017 | Zarins et al. |
| 9,782,099 | B2 | 10/2017 | Williams et al. |
| 9,795,442 | B2 | 10/2017 | Salahieh et al. |
| 9,801,681 | B2 | 10/2017 | Laske et al. |
| 9,808,304 | B2 | 11/2017 | Lalonde |
| 9,861,802 | B2 | 1/2018 | Mickelsen |
| 9,913,685 | B2 | 3/2018 | Clark et al. |
| 9,931,487 | B2 | 4/2018 | Quinn et al. |
| 9,980,652 | B2 | 5/2018 | Govari et al. |
| 9,987,081 | B1 | 6/2018 | Bowers et al. |
| 9,999,465 | B2 | 6/2018 | Long et al. |
| 10,010,368 | B2 | 7/2018 | Laske et al. |
| 10,016,232 | B1 | 7/2018 | Bowers et al. |
| 10,130,419 | B2 | 11/2018 | Deno et al. |
| 10,130,423 | B1 | 11/2018 | Viswanathan et al. |
| 10,172,673 | B2 | 1/2019 | Viswanathan et al. |
| 10,194,818 | B2 | 2/2019 | Williams et al. |
| 10,201,388 | B2 | 2/2019 | Fish et al. |
| 10,238,447 | B2 | 3/2019 | Neal et al. |
| 10,285,755 | B2 | 5/2019 | Stewart et al. |
| 10,322,286 | B2 | 6/2019 | Viswanathan et al. |
| 10,349,824 | B2 | 7/2019 | Claude et al. |
| 10,433,906 | B2 | 10/2019 | Mickelsen |
| 10,433,908 | B2 | 10/2019 | Viswanathan et al. |
| 10,512,505 | B2 | 12/2019 | Raju |
| 10,512,779 | B2 | 12/2019 | Viswanathan et al. |
| 10,517,672 | B2 | 12/2019 | Long |
| 10,617,467 | B2 | 4/2020 | Viswanathan et al. |
| 10,660,702 | B2 | 5/2020 | Viswanathan et al. |
| 10,675,086 | B2 | 6/2020 | Afonso et al. |
| 10,702,326 | B2 | 7/2020 | Neal et al. |
| 10,792,087 | B2 | 10/2020 | Altmann et al. |
| 10,792,097 | B2 | 10/2020 | Ziv-Ari et al. |
| 10,842,572 | B1 * | 11/2020 | Viswanathan ......... A61B 90/36 |
| 10,856,771 | B2 | 12/2020 | Bar-Tal et al. |
| 10,881,455 | B2 | 1/2021 | Schwartz et al. |
| 10,888,373 | B2 | 1/2021 | Koblish et al. |
| 10,893,903 | B2 | 1/2021 | Koblish et al. |
| 11,039,888 | B2 | 6/2021 | Schwartz et al. |
| 11,116,585 | B2 | 9/2021 | Lyons et al. |
| 11,135,008 | B2 | 10/2021 | Govari et al. |
| 11,324,550 | B2 | 5/2022 | Deno et al. |
| 11,369,428 | B2 | 6/2022 | Laughner et al. |
| 11,596,471 | B2 | 3/2023 | Schroeder |
| 11,617,618 | B2 | 4/2023 | Koblish et al. |
| 11,622,713 | B2 | 4/2023 | Ben-Haim et al. |
| 11,737,817 | B2 | 8/2023 | Lyons et al. |
| 11,744,515 | B2 | 9/2023 | Rodriguez et al. |
| 11,793,576 | B2 | 10/2023 | Schwartz et al. |
| 11,890,046 | B2 | 2/2024 | Neal et al. |
| 12,023,091 | B2 | 7/2024 | Schwartz et al. |
| 12,076,131 | B2 | 9/2024 | Osadchy et al. |
| 12,201,352 | B2 | 1/2025 | Deno et al. |
| 2001/0000791 | A1 | 5/2001 | Suorsa et al. |
| 2001/0007070 | A1 | 7/2001 | Stewart et al. |
| 2001/0044624 | A1 | 11/2001 | Seraj et al. |
| 2002/0022839 | A1 | 2/2002 | Stewart et al. |
| 2002/0052602 | A1 | 5/2002 | Wang et al. |
| 2002/0058933 | A1 | 5/2002 | Christopherson et al. |
| 2002/0077627 | A1 | 6/2002 | Johnson et al. |
| 2002/0087169 | A1 | 7/2002 | Brock et al. |
| 2002/0091384 | A1 | 7/2002 | Hooven et al. |
| 2002/0095176 | A1 | 7/2002 | Prestel |
| 2002/0111618 | A1 | 8/2002 | Stewart et al. |
| 2002/0156526 | A1 | 10/2002 | Hlavka et al. |
| 2002/0161323 | A1 | 10/2002 | Miller et al. |
| 2002/0169445 | A1 | 11/2002 | Jain et al. |
| 2002/0177765 | A1 | 11/2002 | Bowe et al. |
| 2002/0183638 | A1 | 12/2002 | Swanson |
| 2003/0014098 | A1 | 1/2003 | Quijano et al. |
| 2003/0018374 | A1 | 1/2003 | Paulos |
| 2003/0023287 | A1 | 1/2003 | Edwards et al. |
| 2003/0028189 | A1 | 2/2003 | Woloszko et al. |
| 2003/0050637 | A1 | 3/2003 | Maguire et al. |
| 2003/0060856 | A1 | 3/2003 | Chornenky et al. |
| 2003/0114849 | A1 | 6/2003 | Ryan |
| 2003/0125729 | A1 | 7/2003 | Hooven et al. |
| 2003/0130598 | A1 | 7/2003 | Manning et al. |
| 2003/0130711 | A1 | 7/2003 | Pearson et al. |
| 2003/0204161 | A1 | 10/2003 | Ferek-Petric |
| 2003/0229379 | A1 | 12/2003 | Maynard |
| 2004/0039382 | A1 | 2/2004 | Kroll et al. |
| 2004/0049181 | A1 | 3/2004 | Stewart et al. |
| 2004/0049182 | A1 | 3/2004 | Koblish et al. |
| 2004/0082859 | A1 | 4/2004 | Schaer |
| 2004/0082948 | A1 | 4/2004 | Stewart et al. |
| 2004/0087939 | A1 | 5/2004 | Eggers et al. |
| 2004/0111087 | A1 | 6/2004 | Stern et al. |
| 2004/0199157 | A1 | 10/2004 | Palanker et al. |
| 2004/0231683 | A1 | 11/2004 | Eng et al. |
| 2004/0236360 | A1 | 11/2004 | Cohn et al. |
| 2004/0254607 | A1 | 12/2004 | Wittenberger et al. |
| 2004/0267337 | A1 | 12/2004 | Hayzelden |
| 2005/0033282 | A1 | 2/2005 | Hooven |
| 2005/0187545 | A1 | 8/2005 | Hooven et al. |
| 2005/0222632 | A1 | 10/2005 | Obino |
| 2005/0251130 | A1 | 11/2005 | Boveja et al. |
| 2005/0261672 | A1 | 11/2005 | Deem et al. |
| 2006/0009755 | A1 | 1/2006 | Sra |
| 2006/0009759 | A1 | 1/2006 | Chrisitian et al. |
| 2006/0015095 | A1 | 1/2006 | Desinger et al. |
| 2006/0015165 | A1 | 1/2006 | Bertolero et al. |
| 2006/0024359 | A1 | 2/2006 | Walker et al. |
| 2006/0058781 | A1 | 3/2006 | Long |
| 2006/0111702 | A1 | 5/2006 | Oral et al. |
| 2006/0142801 | A1 | 6/2006 | Demarais et al. |
| 2006/0167448 | A1 | 7/2006 | Kozel |
| 2006/0217703 | A1 | 9/2006 | Chornenky et al. |
| 2006/0241734 | A1 | 10/2006 | Marshall et al. |
| 2006/0264752 | A1 | 11/2006 | Rubinsky et al. |
| 2006/0270900 | A1 | 11/2006 | Chin et al. |
| 2006/0287648 | A1 | 12/2006 | Schwartz |
| 2006/0293730 | A1 | 12/2006 | Rubinsky et al. |
| 2006/0293731 | A1 | 12/2006 | Rubinsky et al. |
| 2007/0005053 | A1 | 1/2007 | Dando |
| 2007/0021744 | A1 | 1/2007 | Creighton |
| 2007/0060989 | A1 | 3/2007 | Deem et al. |
| 2007/0066972 | A1 | 3/2007 | Ormsby et al. |
| 2007/0129721 | A1 | 6/2007 | Phan et al. |
| 2007/0129760 | A1 | 6/2007 | Demarais et al. |
| 2007/0156135 | A1 | 7/2007 | Rubinsky et al. |
| 2007/0167740 | A1 | 7/2007 | Grunewald et al. |
| 2007/0167940 | A1 | 7/2007 | Stevens-Wright |
| 2007/0173878 | A1 | 7/2007 | Heuser |
| 2007/0208329 | A1 | 9/2007 | Ward et al. |
| 2007/0225589 | A1 | 9/2007 | Viswanathan |
| 2007/0249923 | A1 | 10/2007 | Keenan |
| 2007/0260223 | A1 | 11/2007 | Scheibe et al. |
| 2007/0270792 | A1 | 11/2007 | Hennemann et al. |
| 2008/0009855 | A1 | 1/2008 | Hamou |
| 2008/0033426 | A1 | 2/2008 | Machell |
| 2008/0065061 | A1 | 3/2008 | Viswanathan |
| 2008/0086120 | A1 | 4/2008 | Mirza et al. |
| 2008/0091195 | A1 | 4/2008 | Sliwa et al. |
| 2008/0103545 | A1 | 5/2008 | Bolea et al. |

(56) References Cited

U.S. PATENT DOCUMENTS

2008/0132885 A1 6/2008 Rubinsky et al.
2008/0161789 A1 7/2008 Thao et al.
2008/0172048 A1 7/2008 Martin et al.
2008/0200913 A1 8/2008 Viswanathan
2008/0208118 A1 8/2008 Goldman
2008/0243214 A1 10/2008 Koblish
2008/0275440 A1 11/2008 Kratoska et al.
2008/0281322 A1 11/2008 Sherman et al.
2008/0300574 A1 12/2008 Belson et al.
2008/0300588 A1 12/2008 Groth et al.
2009/0024084 A1 1/2009 Khosla et al.
2009/0048591 A1 2/2009 Ibrahim et al.
2009/0062788 A1 3/2009 Long et al.
2009/0076496 A1 3/2009 Azure
2009/0076500 A1 3/2009 Azure
2009/0105654 A1 4/2009 Kurth et al.
2009/0138009 A1 5/2009 Viswanathan et al.
2009/0149917 A1 6/2009 Whitehurst et al.
2009/0163905 A1 6/2009 Winkler et al.
2009/0177111 A1 7/2009 Miller et al.
2009/0228003 A1 9/2009 Sinelnikov
2009/0240248 A1 9/2009 Deford et al.
2009/0275827 A1 11/2009 Aiken et al.
2009/0281477 A1 11/2009 Mikus et al.
2009/0306651 A1 12/2009 Schneider
2010/0004623 A1 1/2010 Hamilton et al.
2010/0023004 A1 1/2010 Francischelli et al.
2010/0137861 A1 6/2010 Soroff et al.
2010/0185140 A1 7/2010 Kassab et al.
2010/0185186 A1 7/2010 Longoria
2010/0191112 A1 7/2010 Demarais et al.
2010/0191232 A1 7/2010 Boveda
2010/0241185 A1 9/2010 Mahapatra et al.
2010/0249771 A1 9/2010 Pearson et al.
2010/0261994 A1 10/2010 Davalos et al.
2010/0274238 A1 10/2010 Klimovitch
2010/0280513 A1 11/2010 Juergen et al.
2010/0280539 A1 11/2010 Miyoshi et al.
2010/0292687 A1 11/2010 Kauphusman et al.
2010/0312096 A1 12/2010 Guttman et al.
2010/0312300 A1 12/2010 Ryu et al.
2011/0028962 A1 2/2011 Werneth et al.
2011/0028964 A1 2/2011 Edwards
2011/0040199 A1 2/2011 Hopenfeld
2011/0098694 A1 4/2011 Long
2011/0106221 A1 5/2011 Neal et al.
2011/0130708 A1 6/2011 Perry et al.
2011/0144524 A1 6/2011 Fish et al.
2011/0144633 A1 6/2011 Govari
2011/0160785 A1 6/2011 Mori et al.
2011/0190659 A1 8/2011 Long et al.
2011/0190727 A1 8/2011 Edmunds et al.
2011/0213231 A1 9/2011 Hall et al.
2011/0276047 A1 11/2011 Sklar et al.
2011/0276075 A1 11/2011 Fung et al.
2011/0288544 A1 11/2011 Verin et al.
2011/0288547 A1 11/2011 Morgan et al.
2011/0313417 A1 12/2011 De et al.
2012/0029512 A1 2/2012 Willard et al.
2012/0046570 A1 2/2012 Villegas et al.
2012/0053581 A1 3/2012 Wittkampf et al.
2012/0059255 A1 3/2012 Paul et al.
2012/0071872 A1 3/2012 Rubinsky et al.
2012/0078320 A1 3/2012 Schotzko et al.
2012/0078343 A1 3/2012 Fish
2012/0089089 A1 4/2012 Swain et al.
2012/0095459 A1 4/2012 Callas et al.
2012/0101413 A1 4/2012 Beetel et al.
2012/0158021 A1 6/2012 Morrill
2012/0165667 A1 6/2012 Altmann et al.
2012/0172859 A1 7/2012 Condie et al.
2012/0172867 A1 7/2012 Ryu et al.
2012/0197100 A1 8/2012 Razavi et al.
2012/0209260 A1 8/2012 Lambert et al.
2012/0220998 A1 8/2012 Long et al.
2012/0265198 A1 10/2012 Crow et al.
2012/0283582 A1 11/2012 Mahapatra et al.
2012/0303019 A1 11/2012 Zhao et al.
2012/0310052 A1 12/2012 Mahapatra et al.
2012/0310230 A1 12/2012 Willis
2012/0310237 A1 12/2012 Swanson
2012/0316557 A1 12/2012 Sartor et al.
2013/0030430 A1 1/2013 Stewart et al.
2013/0060247 A1 3/2013 Sklar et al.
2013/0060248 A1 3/2013 Sklar et al.
2013/0079768 A1 3/2013 De et al.
2013/0090651 A1 4/2013 Smith
2013/0096655 A1 4/2013 Moffitt et al.
2013/0103027 A1 4/2013 Sklar et al.
2013/0103064 A1 4/2013 Arenson et al.
2013/0131662 A1 5/2013 Wittkampf
2013/0158538 A1 6/2013 Govari
2013/0158621 A1 6/2013 Ding et al.
2013/0172715 A1 7/2013 Just et al.
2013/0172864 A1 7/2013 Ibrahim et al.
2013/0172875 A1 7/2013 Govari et al.
2013/0184702 A1 7/2013 Neal et al.
2013/0218157 A1 8/2013 Callas et al.
2013/0226174 A1 8/2013 Ibrahim et al.
2013/0237984 A1 9/2013 Sklar
2013/0253415 A1 9/2013 Sano et al.
2013/0296679 A1 11/2013 Condie et al.
2013/0310829 A1 11/2013 Cohen
2013/0317385 A1 11/2013 Sklar et al.
2013/0331831 A1 12/2013 Werneth et al.
2013/0338467 A1 12/2013 Grasse et al.
2014/0005664 A1 1/2014 Govari et al.
2014/0024911 A1 1/2014 Harlev et al.
2014/0039288 A1 2/2014 Hue-Teh
2014/0051993 A1 2/2014 Mcgee
2014/0052118 A1 2/2014 Laske et al.
2014/0052126 A1 2/2014 Long et al.
2014/0052216 A1 2/2014 Long et al.
2014/0058377 A1 2/2014 Deem et al.
2014/0081113 A1 3/2014 Cohen et al.
2014/0100563 A1 4/2014 Govari et al.
2014/0107644 A1 4/2014 Falwell et al.
2014/0142408 A1 5/2014 De et al.
2014/0148804 A1 5/2014 Ward et al.
2014/0163480 A1 6/2014 Govari et al.
2014/0163546 A1 6/2014 Govari et al.
2014/0171942 A1 6/2014 Werneth et al.
2014/0180035 A1 6/2014 Anderson
2014/0187916 A1 7/2014 Clark et al.
2014/0194716 A1 7/2014 Diep et al.
2014/0194867 A1 7/2014 Fish et al.
2014/0200567 A1 7/2014 Cox et al.
2014/0235986 A1 8/2014 Harlev et al.
2014/0235988 A1 8/2014 Ghosh
2014/0235989 A1 8/2014 Wodlinger et al.
2014/0243851 A1 8/2014 Cohen et al.
2014/0253140 A1 9/2014 Gilbert
2014/0276760 A1 9/2014 Bonyak et al.
2014/0276782 A1 9/2014 Paskar
2014/0276791 A1 9/2014 Ku et al.
2014/0288556 A1 9/2014 Ibrahim et al.
2014/0303721 A1 10/2014 Fung et al.
2014/0343549 A1 11/2014 Spear et al.
2014/0364845 A1 12/2014 Rashidi
2014/0371613 A1 12/2014 Narayan et al.
2015/0005767 A1 1/2015 Werneth et al.
2015/0011995 A1 1/2015 Avitall et al.
2015/0066108 A1 3/2015 Shi et al.
2015/0119674 A1 4/2015 Fischell et al.
2015/0126840 A1 5/2015 Thakur et al.
2015/0133914 A1 5/2015 Koblish
2015/0138977 A1 5/2015 Dacosta
2015/0141978 A1 5/2015 Subramaniam et al.
2015/0141982 A1 5/2015 Lee
2015/0142041 A1 5/2015 Kendale et al.
2015/0148796 A1 5/2015 Bencini
2015/0150472 A1 6/2015 Harlev et al.
2015/0157402 A1 6/2015 Kunis et al.
2015/0157412 A1 6/2015 Wallace et al.

(56) References Cited

U.S. PATENT DOCUMENTS

2015/0164584 A1 6/2015 Davalos et al.
2015/0173824 A1 6/2015 Davalos et al.
2015/0173828 A1 6/2015 Avitall
2015/0174404 A1 6/2015 Rousso et al.
2015/0182740 A1 7/2015 Mickelsen
2015/0196217 A1 7/2015 Harlev et al.
2015/0223726 A1 8/2015 Harlev et al.
2015/0230699 A1 8/2015 Berul et al.
2015/0258344 A1 9/2015 Tandri et al.
2015/0265342 A1 9/2015 Long et al.
2015/0265344 A1 9/2015 Aktas et al.
2015/0272656 A1 10/2015 Chen
2015/0272664 A9 10/2015 Cohen
2015/0272667 A1 10/2015 Govari et al.
2015/0282729 A1 10/2015 Harlev et al.
2015/0289923 A1 10/2015 Davalos et al.
2015/0304879 A1 10/2015 Dacosta
2015/0320481 A1 11/2015 Cosman et al.
2015/0321021 A1 11/2015 Tandri et al.
2015/0342532 A1 12/2015 Basu et al.
2015/0343212 A1 12/2015 Rousso et al.
2015/0351836 A1 12/2015 Prutchi
2015/0359583 A1 12/2015 Swanson
2016/0000500 A1 1/2016 Salahieh et al.
2016/0008061 A1 1/2016 Fung et al.
2016/0008065 A1 1/2016 Gliner et al.
2016/0029960 A1 2/2016 Toth et al.
2016/0038772 A1 2/2016 Thapliyal et al.
2016/0051204 A1 2/2016 Harlev et al.
2016/0051324 A1 2/2016 Stewart et al.
2016/0058493 A1 3/2016 Neal et al.
2016/0058506 A1 3/2016 Spence et al.
2016/0066993 A1 3/2016 Avitall et al.
2016/0074679 A1 3/2016 Thapliyal et al.
2016/0095531 A1 4/2016 Narayan et al.
2016/0095642 A1 4/2016 Deno et al.
2016/0095653 A1 4/2016 Lambert et al.
2016/0100797 A1 4/2016 Mahapatra et al.
2016/0100884 A1 4/2016 Fay et al.
2016/0106498 A1 4/2016 Highsmith et al.
2016/0106500 A1 4/2016 Olson
2016/0113709 A1 4/2016 Maor
2016/0113712 A1 4/2016 Cheung et al.
2016/0120564 A1 5/2016 Kirkpatrick et al.
2016/0128770 A1 5/2016 Afonso et al.
2016/0166167 A1 6/2016 Narayan et al.
2016/0166310 A1 6/2016 Stewart et al.
2016/0166311 A1 6/2016 Long et al.
2016/0174865 A1 6/2016 Stewart et al.
2016/0183877 A1 6/2016 Williams et al.
2016/0184003 A1 6/2016 Srimathveeravalli et al.
2016/0184004 A1 6/2016 Hull et al.
2016/0213282 A1 7/2016 Leo et al.
2016/0220307 A1 8/2016 Miller et al.
2016/0235470 A1 8/2016 Callas et al.
2016/0249972 A1 9/2016 Klink
2016/0256682 A1 9/2016 Paul et al.
2016/0287314 A1 10/2016 Arena et al.
2016/0310211 A1 10/2016 Long
2016/0324564 A1 11/2016 Gerlach et al.
2016/0324573 A1 11/2016 Mickelson et al.
2016/0331441 A1 11/2016 Konings
2016/0331459 A1 11/2016 Townley et al.
2016/0338770 A1 11/2016 Bar-Tal et al.
2016/0354142 A1 12/2016 Pearson et al.
2016/0361109 A1 12/2016 Weaver et al.
2017/0001016 A1 1/2017 De Ridder
2017/0035499 A1 2/2017 Stewart et al.
2017/0042449 A1 2/2017 Deno et al.
2017/0042615 A1 2/2017 Salahieh et al.
2017/0056648 A1 3/2017 Syed et al.
2017/0065330 A1 3/2017 Mickelsen et al.
2017/0065339 A1 3/2017 Mickelsen
2017/0065340 A1 3/2017 Long
2017/0065343 A1 3/2017 Mickelsen
2017/0071543 A1 3/2017 Basu et al.
2017/0095291 A1 4/2017 Harrington et al.
2017/0105793 A1 4/2017 Cao et al.
2017/0120048 A1 5/2017 He et al.
2017/0146584 A1 5/2017 Daw et al.
2017/0151014 A1 6/2017 Perfler
2017/0151029 A1 6/2017 Mickelsen
2017/0172654 A1 6/2017 Wittkampf et al.
2017/0181795 A1 6/2017 Debruyne
2017/0189097 A1 7/2017 Viswanathan et al.
2017/0215953 A1 8/2017 Long et al.
2017/0245928 A1 8/2017 Xiao et al.
2017/0246455 A1 8/2017 Athos et al.
2017/0312024 A1 11/2017 Harlev et al.
2017/0312025 A1 11/2017 Harlev et al.
2017/0312027 A1 11/2017 Harlev et al.
2018/0001056 A1 1/2018 Leeflang et al.
2018/0028252 A1 2/2018 Lalonde
2018/0042674 A1 2/2018 Mickelsen
2018/0042675 A1 2/2018 Long
2018/0043153 A1 2/2018 Viswanathan et al.
2018/0064488 A1 3/2018 Long et al.
2018/0078218 A1 3/2018 Moisa et al.
2018/0085160 A1 3/2018 Viswanathan et al.
2018/0093088 A1 4/2018 Mickelsen
2018/0125575 A1* 5/2018 Schwartz ............... G16H 10/60
2018/0133460 A1 5/2018 Townley et al.
2018/0161093 A1 6/2018 Basu et al.
2018/0168511 A1 6/2018 Hall et al.
2018/0184982 A1 7/2018 Basu et al.
2018/0193090 A1 7/2018 De et al.
2018/0200497 A1 7/2018 Mickelsen
2018/0235496 A1 8/2018 Wu et al.
2018/0256109 A1 9/2018 Wu et al.
2018/0280080 A1 10/2018 Govari et al.
2018/0303488 A1 10/2018 Hill
2018/0303543 A1 10/2018 Stewart et al.
2018/0311497 A1 11/2018 Viswanathan et al.
2018/0344202 A1 12/2018 Bar-Tal et al.
2018/0344393 A1 12/2018 Gruba et al.
2018/0360531 A1 12/2018 Holmes et al.
2018/0360534 A1 12/2018 Teplitsky et al.
2019/0015007 A1 1/2019 Rottmann et al.
2019/0015638 A1 1/2019 Gruba et al.
2019/0029749 A1 1/2019 Garcia et al.
2019/0030328 A1 1/2019 Stewart et al.
2019/0046791 A1 2/2019 Ebbers et al.
2019/0069950 A1 3/2019 Viswanathan et al.
2019/0076179 A1 3/2019 Babkin et al.
2019/0125439 A1 5/2019 Rohl et al.
2019/0125788 A1 5/2019 Gruba et al.
2019/0143106 A1 5/2019 Dewitt et al.
2019/0151015 A1 5/2019 Viswanathan et al.
2019/0175263 A1 6/2019 Altmann et al.
2019/0183378 A1 6/2019 Mosesov et al.
2019/0183567 A1 6/2019 Govari et al.
2019/0192223 A1 6/2019 Rankin
2019/0201089 A1 7/2019 Waldstreicher et al.
2019/0201688 A1 7/2019 Olson
2019/0209235 A1 7/2019 Stewart et al.
2019/0223948 A1 7/2019 Stewart et al.
2019/0231421 A1 8/2019 Viswanathan et al.
2019/0231425 A1 8/2019 Waldstreicher et al.
2019/0254564 A1 8/2019 Schwartz et al.
2019/0254735 A1 8/2019 Stewart et al.
2019/0269912 A1 9/2019 Viswanathan et al.
2019/0298442 A1 10/2019 Ogata et al.
2019/0307500 A1 10/2019 Byrd et al.
2019/0350647 A1 11/2019 Ramberg et al.
2019/0350649 A1 11/2019 Sutermeister et al.
2019/0376055 A1 12/2019 Davalos et al.
2020/0008869 A1 1/2020 Byrd
2020/0008870 A1 1/2020 Gruba et al.
2020/0009378 A1 1/2020 Stewart et al.
2020/0038104 A1 2/2020 Mickelsen
2020/0046423 A1 2/2020 Viswanathan et al.
2020/0093539 A1 3/2020 Long et al.
2020/0155228 A1 5/2020 Salehi et al.
2020/0297415 A1 9/2020 Marshik et al.

(56) References Cited

U.S. PATENT DOCUMENTS

| | | | | |
|---|---|---|---|---|
| 2020/0345304 | A1 | 11/2020 | Joshi et al. | |
| 2021/0169394 | A1 | 6/2021 | Chou et al. | |
| 2021/0393327 | A1* | 12/2021 | Eyster | A61B 18/1492 |
| 2022/0133405 | A1 | 5/2022 | Mickelsen | |
| 2022/0361941 | A1* | 11/2022 | Townley | A61B 18/1485 |
| 2022/0401146 | A1 | 12/2022 | Asconeguy et al. | |
| 2023/0148138 | A1* | 5/2023 | Hautvast et al. | A61B 18/14 606/1 |
| 2024/0173063 | A1* | 5/2024 | Neal, II | A61B 34/10 |
| 2024/0225724 | A9 | 7/2024 | Govari | |
| 2025/0387160 | A1 | 12/2025 | Laughner et al. | |

FOREIGN PATENT DOCUMENTS

| | | | | |
|---|---|---|---|---|
| EP | 1125549 | A2 | 8/2001 | |
| EP | 0797956 | B1 | 6/2003 | |
| EP | 1340469 | A1 | 9/2003 | |
| EP | 1127552 | B1 | 6/2006 | |
| EP | 1803411 | A2 | 7/2007 | |
| EP | 1009303 | B1 | 6/2009 | |
| EP | 2213729 | A2 | 8/2010 | |
| EP | 2382935 | A1 | 11/2011 | |
| EP | 2425871 | A2 | 3/2012 | |
| EP | 2532320 | A2 | 12/2012 | |
| EP | 2587275 | A1 | 5/2013 | |
| EP | 2663227 | A1 | 11/2013 | |
| EP | 1909678 | B1 | 1/2014 | |
| EP | 2217165 | B1 | 3/2014 | |
| EP | 2376193 | B1 | 3/2014 | |
| EP | 2708181 | A1 | 3/2014 | |
| EP | 2777579 | A1 | 9/2014 | |
| EP | 2777585 | A1 | 9/2014 | |
| EP | 2934307 | A1 | 10/2015 | |
| EP | 3056242 | A1 | 8/2016 | |
| EP | 3111871 | A1 | 1/2017 | |
| EP | 3151773 | B1 | 4/2018 | |
| JP | 06-507797 | A | 9/1994 | |
| JP | 2000-508196 | A | 7/2000 | |
| JP | 2005-516666 | A | 6/2005 | |
| JP | 2006-506184 | A | 2/2006 | |
| JP | 2008-538997 | A | 11/2008 | |
| JP | 2009-500129 | A | 1/2009 | |
| JP | 2011-509158 | A | 3/2011 | |
| JP | 2012-050538 | A | 3/2012 | |
| WO | 92/07622 | A1 | 5/1992 | |
| WO | 92/21278 | A1 | 12/1992 | |
| WO | 92/21285 | A1 | 12/1992 | |
| WO | 94/07413 | A1 | 4/1994 | |
| WO | 97/24073 | A1 | 7/1997 | |
| WO | 97/25917 | A1 | 7/1997 | |
| WO | 97/37719 | A1 | 10/1997 | |
| WO | 99/04851 | A1 | 2/1999 | |
| WO | 99/22659 | A1 | 5/1999 | |
| WO | 99/56650 | A1 | 11/1999 | |
| WO | 99/59486 | A2 | 11/1999 | |
| WO | 02/56782 | A2 | 7/2002 | |
| WO | 03/53289 | A1 | 7/2003 | |
| WO | 03/65916 | A1 | 8/2003 | |
| WO | 2004/045442 | A1 | 6/2004 | |
| WO | 2004/086994 | A1 | 10/2004 | |
| WO | 2005/046487 | A1 | 5/2005 | |
| WO | 2006/115902 | A2 | 11/2006 | |
| WO | 2007/006055 | A2 | 1/2007 | |
| WO | 2007/079438 | A2 | 7/2007 | |
| WO | 2009/082710 | A1 | 7/2009 | |
| WO | 2009/089343 | A1 | 7/2009 | |
| WO | 2009/137800 | A2 | 11/2009 | |
| WO | 2010/014480 | A1 | 2/2010 | |
| WO | 2011/028310 | A1 | 3/2011 | |
| WO | 2011/154805 | A1 | 12/2011 | |
| WO | 2012/051433 | A2 | 4/2012 | |
| WO | 2012/097067 | A1 | 7/2012 | |
| WO | 2012/153928 | A2 | 11/2012 | |
| WO | 2013/019385 | A1 | 2/2013 | |
| WO | 2014/025394 | A1 | 2/2014 | |
| WO | 2014/031800 | A1 | 2/2014 | |
| WO | 2014/036439 | A2 | 3/2014 | |
| WO | 2014/100579 | A1 | 6/2014 | |
| WO | 2014/160832 | A2 | 10/2014 | |
| WO | 2015/066322 | A1 | 5/2015 | |
| WO | 2015/099786 | A1 | 7/2015 | |
| WO | 2015/103530 | A1 | 7/2015 | |
| WO | 2015/103574 | A1 | 7/2015 | |
| WO | 2015/130824 | A1 | 9/2015 | |
| WO | 2015/140741 | A1 | 9/2015 | |
| WO | 2015/143327 | A1 | 9/2015 | |
| WO | 2015/171921 | A2 | 11/2015 | |
| WO | 2015/175944 | A1 | 11/2015 | |
| WO | 2015/192018 | A1 | 12/2015 | |
| WO | 2015/192027 | A1 | 12/2015 | |
| WO | 2016/059027 | A1 | 4/2016 | |
| WO | 2016/060983 | A1 | 4/2016 | |
| WO | 2016/081650 | A1 | 5/2016 | |
| WO | 2016/090175 | A1 | 6/2016 | |
| WO | 2017/093926 | A1 | 6/2017 | |
| WO | 2017/119934 | A1 | 7/2017 | |
| WO | 2017/120169 | A1 | 7/2017 | |
| WO | 2017/192477 | A1 | 11/2017 | |
| WO | 2017/192495 | A1 | 11/2017 | |
| WO | 2017/201504 | A1 | 11/2017 | |
| WO | 2017/218734 | A1 | 12/2017 | |
| WO | 2018/005511 | A1 | 1/2018 | |
| WO | 2018/106569 | A1 | 6/2018 | |
| WO | 2018/200800 | A1 | 11/2018 | |
| WO | 2019/023259 | A2 | 1/2019 | |
| WO | 2019/023280 | A1 | 1/2019 | |
| WO | 2019/035071 | A1 | 2/2019 | |
| WO | 2019/133608 | A1 | 7/2019 | |
| WO | 2019/136218 | A1 | 7/2019 | |
| WO | WO-2019133606 | A1 * | 7/2019 | A61B 18/1206 |
| WO | 2019/181612 | A1 | 9/2019 | |
| WO | 2019/234133 | A1 | 12/2019 | |
| WO | 2021/078918 | A1 | 4/2021 | |

OTHER PUBLICATIONS

Hobbs, E. P., “Investor Relations Update: Tissue Ablation via Irreversible Electroporation (IRE),” Powerpoint (2004), 16 pages.

International Search Report and Written Opinion received for PCT Patent Application No. PCT/US2021/032501, mailed on Sep. 1, 2021, 18 pages.

Lavee, J. et al., “A Novel Nonthermal Energy Source for Surgical Epicardial Atrial Ablation: Irreversible Electroporation,” The Heart Surgery Forum #2006-1202, 10(2), 2007 [Epub Mar. 2007].

Madhavan, M. et al., “Novel Percutaneous Epicardial Autonomic Modulation in the Canine for Atrial Fibrillation: Results of an Efficacy and Safety Study,” Pace, 00:1-11 (2016).

Neven, K. et al., “Epicardial linear electroporation ablation and lesion size,” Heart Rhythm, 11:1465-1470 (2014).

Neven, K. et al., “Myocardial Lesion Size After Epicardial Electroporation Catheter Ablation After Subxiphoid Puncture,” Circ Arrhythm Electrophysiol., 7(4):728-733 (2014).

Neven, K. et al., “Safety and Feasibility of Closed Chest Epicardial Catheter Ablation Using Electroporation,” Circ Arrhythm Electrophysiol., 7:913-919 (2014).

Van Driel, V.J.H.M. et al., “Low vulnerability of the right phrenic nerve to electroporation ablation,” Heart Rhythm, 12:1838-1844 (2015).

Van Driel, V.J.H.M. et al., “Pulmonary Vein Stenosis After Catheter Ablation Electroporation Versus Radiofrequency,” Circ Arrhythm Electrophysiol., 7(4):734-738 (2014).

Wittkampf, F.H et al., “Feasibility of Electroporation for the Creation of Pulmonary Vein Ostial Lesions,” J Cardiovasc Electrophysiol, 22(3):302-309 (Mar. 2011).

Wittkampf, F.H. et al., “Myocardial Lesion Depth With Circular Electroporation Ablation,” Circ. Arrhythm Electrophysiol., 5(3):581-586 (2012).

* cited by examiner

OVERLAY OF DYNAMIC SPATIAL DATA ON USER INTERFACE FOR ABLATION BY IRREVERSIBLE ELECTROPORATION

CROSS REFERENCE TO RELATED APPLICATION

This application claims priority to Provisional Application No. 63/030,042, filed May 26, 2020, which is herein incorporated by reference in its entirety.

TECHNICAL FIELD

The present disclosure relates to medical systems and methods for ablating tissue in a patient. More specifically, the present disclosure relates to medical systems and methods for ablation of tissue by electroporation.

BACKGROUND

Ablation procedures are used to treat many different conditions in patients. Ablation can be used to treat cardiac arrhythmias, benign tumors, cancerous tumors, and to control bleeding during surgery. Usually, ablation is accomplished through thermal ablation techniques including radio-frequency (RF) ablation and cryoablation. In RF ablation, a probe is inserted into the patient and radio frequency waves are transmitted through the probe to the surrounding tissue. The radio frequency waves generate heat, which destroys surrounding tissue and cauterizes blood vessels. In cryoablation, a hollow needle or cryoprobe is inserted into the patient and cold, thermally conductive fluid is circulated through the probe to freeze and kill the surrounding tissue. RF ablation and cryoablation techniques indiscriminately kill tissue through cell necrosis, which may damage or kill otherwise healthy tissue, such as tissue in the esophagus, phrenic nerve cells, and tissue in the coronary arteries.

Another ablation technique uses electroporation. In electroporation, or electro-permeabilization, an electrical field is applied to cells in order to increase the permeability of the cell membrane. The electroporation can be reversible or irreversible, depending on the strength of the electric field. If the electroporation is reversible, the increased permeability of the cell membrane can be used to introduce chemicals, drugs, and/or deoxyribonucleic acid (DNA) into the cell, prior to the cell healing and recovering. If the electroporation is irreversible, the affected cells are killed through apoptosis.

Irreversible electroporation can be used as a nonthermal ablation technique. In irreversible electroporation, trains of short, high voltage pulses are used to generate electric fields that are strong enough to kill cells through apoptosis. In ablation of cardiac tissue, irreversible electroporation can be a safe and effective alternative to the indiscriminate killing of thermal ablation techniques, such as RF ablation and cryoablation. Irreversible electroporation can be used to kill targeted tissue, such as myocardium tissue, by using an electric field strength and duration that kills the targeted tissue but does not permanently damage other cells or tissue, such as non-targeted myocardium tissue, red blood cells, vascular smooth muscle tissue, endothelium tissue, and nerve cells. Planning irreversible electroporation ablation procedures can be difficult due to the lack of acute visualization or data indicating which tissues have been irreversibly electroporated, as opposed to reversibly electroporated.

Where tissue recovery can occur over minutes, hours, or days after the ablation is completed.

SUMMARY

As recited in examples, Example 1 is a system for ablation by electroporation. The system including a catheter having electrodes, a display, and a controller. The controller to generate, based on models of electric fields, graphical representations of the electric fields that can be produced using the electrodes, and overlay, on the display, the graphical representations of the electric fields and an anatomical map of a patient to aid in planning the ablation by electroporation, prior to delivering energy.

Example 2 is the system of Example 1, wherein the controller is configured to generate the graphical representations of the electric fields based on characteristics of the catheter.

Example 3 is the system of any one of Examples 1 and 2, wherein the controller is configured to include at least one of electric field lines in the graphical representations of the electric fields on the anatomical map and electric field strength threshold lines in the graphical representations of the electric fields on the anatomical map.

Example 4 is the system of any one of Examples 1-3, wherein the controller is configured to include at least one of a reversible electric field strength threshold line in a range of 200-250 volts per centimeter, a critical electric field strength threshold line of 400 volts per centimeter for irreversible electroporation, and an extreme electric field strength threshold line of 1000 volts per centimeter.

Example 5 is the system of any one of Examples 1-4, wherein the controller is configured to include markings where electric field strength threshold lines intersect with surrounding tissue in the graphical representations of the electric fields.

Example 6 is the system of any one of Examples 1-5, wherein the controller is configured to include at least one of a predicted zone of reversible electroporation and a predicted zone of irreversible electroporation in the graphical representations of the electric fields.

Example 7 is the system of any one of Examples 1-6, wherein the controller is configured to include at least one of markings where the electric fields intersect previously created lesions in the graphical representations of the electric fields and a predicted lesion in the graphical representations of the electric fields.

Example 8 is a system for ablation by electroporation. The system including a catheter having electrodes and a controller. The controller to generate models of electric fields based on characteristics of the catheter, generate graphical representations of the electric fields using the models of the electric fields, and display the graphical representations of the electric fields on an anatomical map of a patient to aid in planning the ablation by electroporation, prior to delivering energy.

Example 9 is the system of Example 8, wherein the controller is configured to receive complex tissue impedance information about surrounding tissue to characterize the surrounding tissue and aid in generating the graphical representations of the electric fields.

Example 10 is the system of any one of Examples 8 and 9, wherein the controller is configured to dynamically change the graphical representations of the electric fields based on one or more of: changes in position of the catheter relative to surrounding tissue; changes in the catheter;

changes in pulse parameters to be provided to the electrodes of the catheter; and changes in measured impedance values of the surrounding tissue.

Example 11 is the system of any one of Examples 8-10, wherein the controller is configured to provide one or more of suggested changes to pulse parameters and automatic dynamical changes to the pulse parameters in response to at least one of measured impedance values of the surrounding tissue and changes in the catheter to maintain a critical electric field strength at a location.

Example 12 is a method of planning ablation by electroporation. The method including generating, by a controller and based on models of electric fields, graphical representations of the electric fields that can be produced using electrodes on a catheter, and displaying, on a display, the graphical representations of the electric fields and an anatomical map of a patient to aid in the planning of the ablation by electroporation, prior to delivering energy.

Example 13 is the method of Example 12, comprising displaying at least one of electric field lines in the graphical representations of the electric fields on the anatomical map and electric field strength threshold lines in the graphical representations of the electric fields on the anatomical map.

Example 14 is the method of any one of Examples 12 and 13, comprising one or more of displaying markings where electric field strength threshold lines intersect surrounding tissue, displaying a predicted zone of reversible electroporation, displaying a predicted zone of irreversible electroporation, displaying markings where the electric fields intersect previously created lesions, displaying a predicted lesion on the anatomical map.

Example 15 is the method of any one of Examples 12-14, comprising dynamically changing, by the controller, the graphical representations of the electric fields based on one or more of: changes in position of the catheter relative to surrounding tissue; changes in the catheter; changes in pulse parameters to be provided to the electrodes of the catheter; and changes in measured impedance values of the surrounding tissue.

Example 16 is a system for ablation by electroporation. The system includes a catheter having electrodes, a display, and a controller. The controller is configured to generate, based on models of electric fields, graphical representations of the electric fields that can be produced using the electrodes, and overlay, on the display, the graphical representations of the electric fields and an anatomical map of a patient to aid in planning the ablation by electroporation, prior to delivering energy.

Example 17 is the system of Example 16, wherein the controller is configured to generate the graphical representations of the electric fields based on characteristics of the catheter and a position of the catheter relative to surrounding tissue.

Example 18 is the system of Example 16, wherein the controller is configured to display electric field strength based on electric pulse parameters of electric pulses to be provided to the electrodes of the catheter.

Example 19 is the system of Example 16, wherein the controller is configured to include at least one of electric field lines in the graphical representations of the electric fields on the anatomical map and electric field strength threshold lines in the graphical representations of the electric fields on the anatomical map.

Example 20 is the system of Example 16, wherein the controller is configured to include at least one of a reversible electric field strength threshold line in a range of 200-250 volts per centimeter, a critical electric field strength threshold line of 400 volts per centimeter for irreversible electroporation, and an extreme electric field strength threshold line of 1000 volts per centimeter.

Example 21 is the system of Example 16, wherein the controller is configured to include markings where electric field strength threshold lines intersect with surrounding tissue in the graphical representations of the electric fields.

Example 22 is the system of Example 16, wherein the controller is configured to include at least one of a predicted zone of reversible electroporation and a predicted zone of irreversible electroporation in the graphical representations of the electric fields.

Example 23 is the system of Example 16, wherein the controller is configured to include markings where the electric fields intersect previously created lesions in the graphical representations of the electric fields.

Example 24 is the system of Example 16, wherein the controller is configured to include a predicted lesion in the graphical representations of the electric fields.

Example 25 is a system for ablation by electroporation. The system includes a catheter having electrodes and a controller. The controller is configured to generate models of electric fields based on characteristics of the catheter, generate graphical representations of the electric fields using the models of the electric fields, and display the graphical representations of the electric fields on an anatomical map of a patient to aid in planning the ablation by electroporation, prior to delivering energy.

Example 26 is the system of Example 25, wherein the controller is configured to receive complex tissue impedance information about surrounding tissue to characterize the surrounding tissue and aid in generating the graphical representations of the electric fields.

Example 27 is the system of Example 25, wherein the controller is configured to dynamically change the graphical representations of the electric fields based on one or more of: changes in position of the catheter relative to surrounding tissue; changes in the catheter; changes in pulse parameters to be provided to the electrodes of the catheter; and changes in measured impedance values of the surrounding tissue.

Example 28 is the system of Example 25, wherein the controller is configured to provide one or more of suggested changes to pulse parameters and automatic dynamical changes to the pulse parameters in response to at least one of measured impedance values of the surrounding tissue and changes in the catheter to maintain a critical electric field strength at a location.

Example 29 is the system of Example 25, comprising sensing electrodes on the catheter, wherein the controller is configured to display real-time information from the sensing electrodes and the graphical representations of the electric fields on the anatomical map of the patient to aid the user in optimizing catheter placement, prior to delivering energy.

Example 30 is a method of planning ablation by electroporation. The method includes generating, by a controller and based on models of electric fields, graphical representations of the electric fields that can be produced using electrodes on a catheter, and displaying, on a display, the graphical representations of the electric fields and an anatomical map of a patient to aid in the planning of the ablation by electroporation, prior to delivering energy.

Example 31 is the method of Example 30, wherein generating the graphical representations of the electric fields includes generating the graphical representations of the electric fields based on characteristics of the catheter and a position of the catheter in the patient relative to surrounding tissue.

Example 32 is the method of Example 30, comprising displaying electric field strength based on electric pulse parameters of electric pulses to be provided to the electrodes of the catheter.

Example 33 is the method of Example 30, comprising displaying at least one of electric field lines in the graphical representations of the electric fields on the anatomical map and electric field strength threshold lines in the graphical representations of the electric fields on the anatomical map.

Example 34 is the method of Example 30, comprising one or more of displaying markings where electric field strength threshold lines intersect surrounding tissue, displaying a predicted zone of reversible electroporation, displaying a predicted zone of irreversible electroporation, displaying markings where the electric fields intersect previously created lesions, displaying a predicted lesion on the anatomical map.

Example 35 is the method of Example 30, comprising dynamically changing, by the controller, the graphical representations of the electric fields based on one or more of: changes in position of the catheter relative to surrounding tissue; changes in the catheter; changes in pulse parameters to be provided to the electrodes of the catheter; and changes in measured impedance values of the surrounding tissue.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
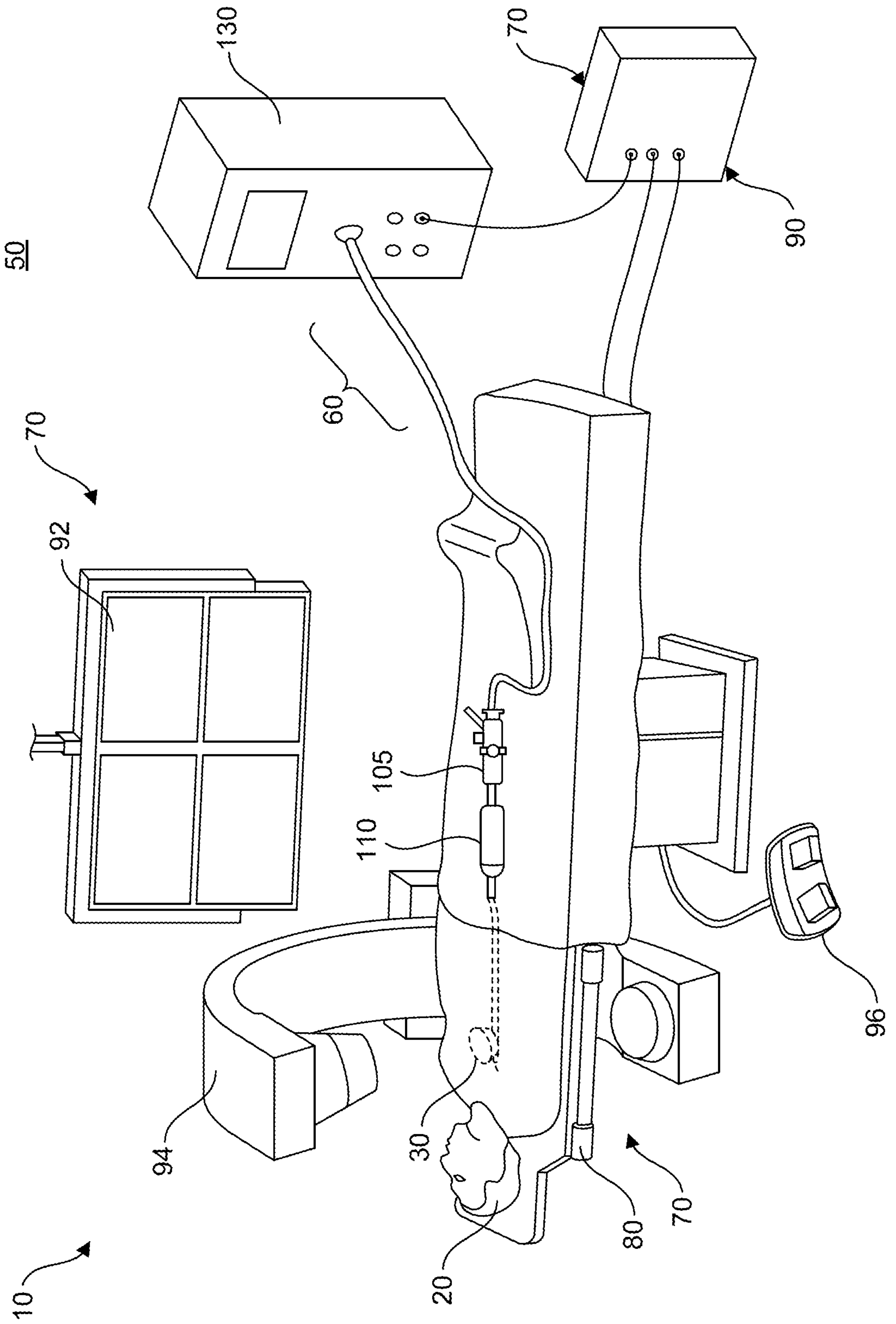
FIG. 1 is a diagram illustrating an exemplary clinical setting for treating a patient, and for treating a heart of the patient, using an electrophysiology system, in accordance with embodiments of the subject matter of the disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

FIG. 1 is a diagram illustrating an exemplary clinical setting 10 for treating a patient 20, and for treating a heart 30 of the patient 20, using an electrophysiology system 50, in accordance with embodiments of the subject matter of the disclosure. The electrophysiology system 50 includes an electroporation catheter system 60 and an electro-anatomical mapping (EAM) system 70, which includes a localization field generator 80, a mapping and navigation controller 90, and a display 92. Also, the clinical setting 10 includes additional equipment such as imaging equipment 94 (represented by the C-arm) and various controller elements, such as a foot controller 96, configured to allow an operator to control various aspects of the electrophysiology system 50. As will be appreciated by the skilled artisan, the clinical setting 10 may have other components and arrangements of components that are not shown in FIG. 1.

The electroporation catheter system 60 includes an electroporation catheter 105, an introducer sheath 110, and an electroporation console 130. Additionally, the electroporation catheter system 60 includes various connecting elements, e.g., cables, umbilicals, and the like, that operate to functionally connect the components of the electroporation catheter system 60 to one another and to the components of the EAM system 70. This arrangement of connecting elements is not of critical importance to the present disclosure, and the skilled artisan will recognize that the various components described herein can be interconnected in a variety of ways.

In embodiments, the electroporation catheter system 60 is configured to deliver electric field energy to targeted tissue in the patient's heart 30 to create tissue apoptosis, rendering the tissue incapable of conducting electrical signals. Also, as will be described in greater detail below, the electroporation catheter system 60 is configured to generate, based on models of electric fields, graphical representations of the electric fields that can be produced using the electroporation catheter 105 and to overlay, on the display 92, the graphical representations of the electric fields on an anatomical map of the patient's heart to aid a user in planning ablation by irreversible electroporation using the electroporation catheter 105, prior to delivering energy. In embodiments, the electroporation catheter system 60 is configured to generate the graphical representations of the electric fields based on characteristics of the electroporation catheter 105 and the position of the electroporation catheter 105 in the patient 20, such as in the heart 30 of the patient 20. In embodiments, the electroporation catheter system 60 is configured to generate the graphical representations of the electric fields based on characteristics of the electroporation catheter 105 and the position of the electroporation catheter 105 in the patient 20, such as in the heart 30 of the patient 20, and the characteristics of the tissue surrounding the catheter 105, such as measured impedances of the tissue.

The electroporation console 130 is configured to control functional aspects of the electroporation catheter system 60. In embodiments, the electroporation console 130 is configured to provide one or more of the following: modeling the electric fields that can be generated by the electroporation catheter 105, which often includes consideration of the physical characteristics of the electroporation catheter 105 including the electrodes and spatial relationships of the electrodes on the electroporation catheter 105; generating the graphical representations of the electric fields, which often includes consideration of the position of the electroporation catheter 105 in the patient 20 and characteristics of the surrounding tissue; and overlaying, on the display 92, the generated graphical representations on an anatomical map. In some embodiments, the electroporation control console 130 is configured to generate the anatomical map. In some embodiments, the EAM system 70 is configured to generate the anatomical map for display on the display 92.

In embodiments, the electroporation console 130 includes one or more controllers, microprocessors, and/or computers that execute code out of memory to control and/or perform the functional aspects of the electroporation catheter system 60. In embodiments, the memory can be part of the one or more controllers, microprocessors, and/or computers, and/or part of memory capacity accessible through a network, such as the world wide web.

In embodiments, the introducer sheath 110 is operable to provide a delivery conduit through which the electroporation catheter 105 can be deployed to the specific target sites within the patient's heart 30.

The EAM system 70 is operable to track the location of the various functional components of the electroporation catheter system 60, and to generate high-fidelity three-dimensional anatomical and electro-anatomical maps of the cardiac chambers of interest. In embodiments, the EAM system 70 can be the RHYTHMIA™ HDx mapping system marketed by Boston Scientific Corporation. Also, in embodiments, the mapping and navigation controller 90 of the EAM system 70 includes one or more controllers, microprocessors, and/or computers that execute code out of memory to control and/or perform functional aspects of the EAM system 70, where the memory, in embodiments, can be part of the one or more controllers, microprocessors, and/or computers, and/or part of memory capacity accessible through a network, such as the world wide web.

As will be appreciated by the skilled artisan, the depiction of the electrophysiology system 50 shown in FIG. 1 is intended to provide a general overview of the various components of the system 50 and is not in any way intended to imply that the disclosure is limited to any set of components or arrangement of the components. For example, the skilled artisan will readily recognize that additional hardware components, e.g., breakout boxes, workstations, and the like, can and likely will be included in the electrophysiology system 50.

The EAM system 70 generates a localization field, via the field generator 80, to define a localization volume about the heart 30, and one or more location sensors or sensing elements on the tracked device(s), e.g., the electroporation catheter 105, generate an output that can be processed by the mapping and navigation controller 90 to track the location of the sensor, and consequently, the corresponding device, within the localization volume. In the illustrated embodiment, the device tracking is accomplished using magnetic tracking techniques, whereby the field generator 80 is a magnetic field generator that generates a magnetic field defining the localization volume, and the location sensors on the tracked devices are magnetic field sensors.

In other embodiments, impedance tracking methodologies may be employed to track the locations of the various devices. In such embodiments, the localization field is an electric field generated, for example, by an external field generator arrangement, e.g., surface electrodes, by intra-body or intra-cardiac devices, e.g., an intracardiac catheter, or both. In these embodiments, the location sensing elements can constitute electrodes on the tracked devices that generate outputs received and processed by the mapping and navigation controller 90 to track the location of the various location sensing electrodes within the localization volume.

In embodiments, the EAM system 70 is equipped for both magnetic and impedance tracking capabilities. In such embodiments, impedance tracking accuracy can, in some instances be enhanced by first creating a map of the electric field induced by the electric field generator within the cardiac chamber of interest using a probe equipped with a magnetic location sensor, as is possible using the aforementioned RHYTHMIA HDx™ mapping system. One exemplary probe is the INTELLAMAP ORION™ mapping catheter marketed by Boston Scientific Corporation.

Regardless of the tracking methodology employed, the EAM system 70 utilizes the location information for the various tracked devices, along with cardiac electrical activity acquired by, for example, the electroporation catheter 105 or another catheter or probe equipped with sensing electrodes, to generate, and display via the display 92, detailed three-dimensional geometric anatomical maps or representations of the cardiac chambers as well as electro-anatomical maps in which cardiac electrical activity of interest is superimposed on the geometric anatomical maps. Furthermore, the EAM system 70 can generate a graphical representation of the various tracked devices within the geometric anatomical map and/or the electro-anatomical map.

Embodiments of the present disclosure integrate the electroporation catheter system 60 with the EAM system 70 to allow graphical representations of the electric fields that can be produced by the electroporation catheter 105 to be visualized on an anatomical map of the patient and, in some embodiments, on an electro-anatomical map of the patient's heart. The integrated system of the present disclosure thus has the capability to enhance the efficiency of clinical workflows, including enhancement of planning the ablation of portions of the patient's heart by irreversible electroporation. Embodiments of the disclosure include generating the graphical representations of the electric fields that can be produced by the electroporation catheter 105, generating the anatomical maps, generating the electro-anatomical maps, and displaying information related to the location and electric field strengths of the electric fields that can be produced by the electroporation catheter 105.

Figure 2A:
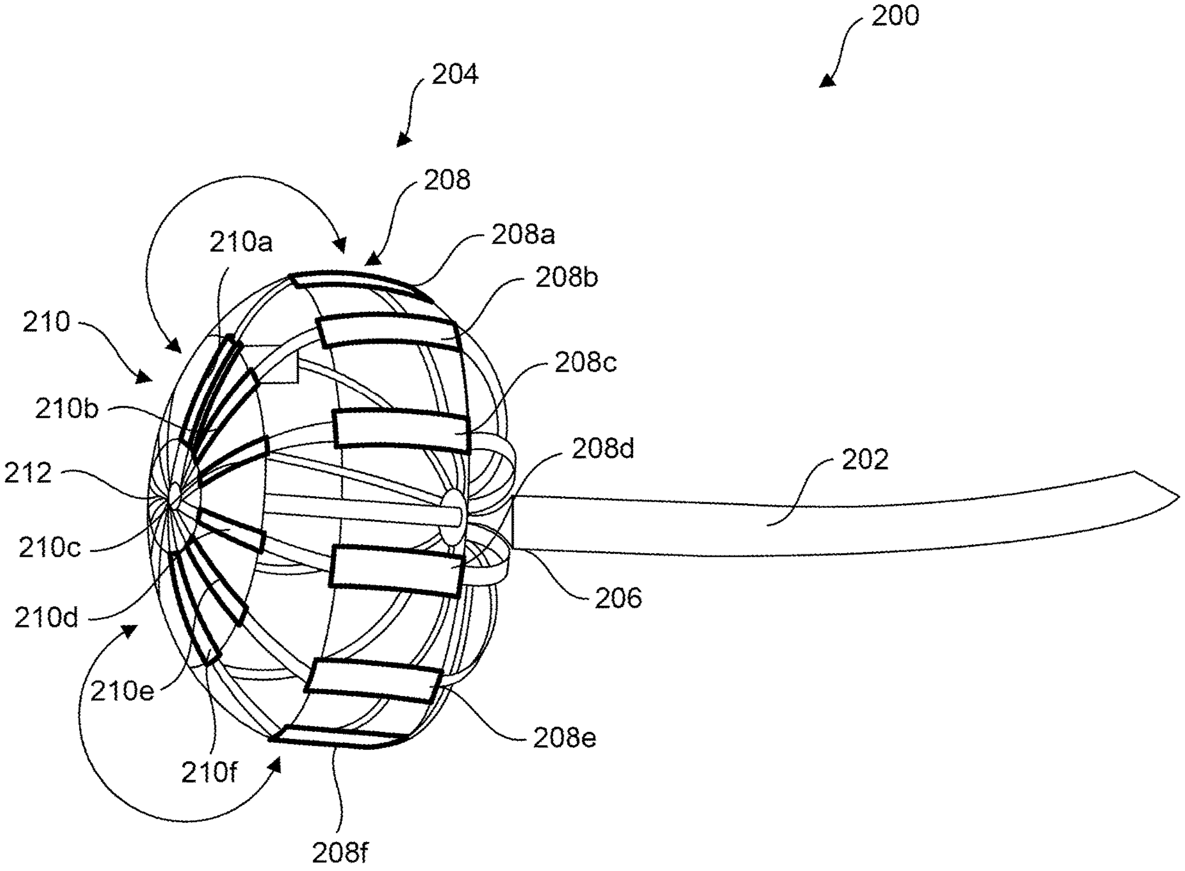
FIG. 2A is a diagram illustrating the catheter, in accordance with embodiments of the subject matter of the disclosure.
Figure 2B:
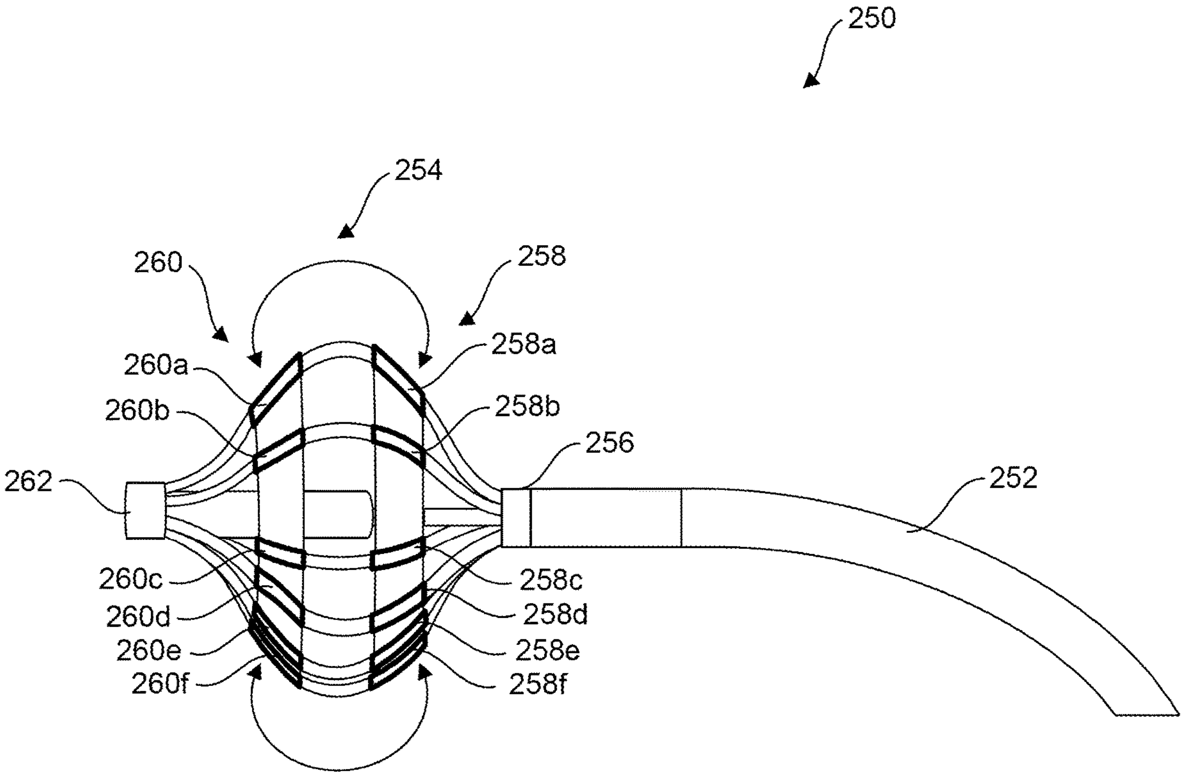
FIG. 2B is a diagram illustrating the catheter, in accordance with embodiments of the subject matter of the disclosure.

FIGS. 2A and 2B are diagrams illustrating catheters 200 and 250 that can be used for electroporation, including ablation by irreversible electroporation, in accordance with embodiments of the subject matter of the disclosure. The catheters 200 and 250 include electrodes, as described below, that are spaced apart from one another and configured to conduct electricity. Catheter characteristics are used to model electric fields that can be produced by the catheter. In embodiments, the characteristics used to model the electric fields can include: the type of catheter, such as a basket catheter that has a constant profile after being opened and a spline catheter that has a variable profile, which can be opened and closed by degree; the form factor of the catheter, such as a balloon catheter, a basket catheter, and a spline catheter; the number of electrodes; the inter-electrode spacing on the catheter; the spatial relationships and orientation of the electrodes, especially in relation to other electrodes on the same catheter; the type of material that the electrodes are made of; and the shape of the electrodes. In embodiments, the type of catheter and/or the form factor of the catheter includes catheters, such as linear ablation catheters and focal ablation catheters. Where, the type of catheter and/or the form factor of the catheter is not limited to those mentioned herein.

FIG. 2A is a diagram illustrating the catheter 200, in accordance with embodiments of the subject matter of the disclosure. The catheter 200 includes a catheter shaft 202 and a catheter basket 204 connected to the catheter shaft 202 at the distal end 206 of the catheter shaft 202. The catheter basket 204 includes a first group of electrodes 208 disposed at the circumference of the catheter basket 204 and a second group of electrodes 210 disposed adjacent the distal end 212 of the catheter basket 204. Each of the electrodes in the first group of electrodes 208 and each of the electrodes in the second group of electrodes 210 is configured to conduct electricity and to be operably connected to the electroporation console 130. In embodiments, one or more of the electrodes in the first group of electrodes 208 and the second group of electrodes 210 includes metal.

Electrodes in the first group of electrodes 208 are spaced apart from electrodes in the second group of electrodes 210. The first group of electrodes 208 includes electrodes 208*a*-208*f* and the second group of electrodes 210 includes electrodes 210*a*-210*f*. Also, electrodes in the first group of electrodes 208, such as electrodes 208*a*-208*f*, are spaced apart from one another and electrodes in the second of electrodes 210, such as electrodes 210*a*-210*f*, are spaced apart from one another.

The spatial relationships and orientation of the electrodes in the first group of electrodes 208 and the spatial relationships and orientation of the electrodes in the second group of electrodes 210 in relation to other electrodes on the same catheter 200 is known or can be determined. In embodiments, the spatial relationships and orientation of the electrodes in the first group of electrodes 208 and the spatial relationships and orientation of the electrodes in the second group of electrodes 210 in relation to other electrodes on the same catheter 200 is constant, once the catheter is deployed.

As to electric fields, in embodiments, each of the electrodes in the first group of electrodes 208 and each of the electrodes in the second group of electrodes 210 can be selected to be an anode or a cathode, such that electric fields can be set up between any two or more of the electrodes in the first and second groups of electrodes 208 and 210. Also, in embodiments, each of the electrodes in the first group of electrodes 208 and each of the electrodes in the second group of electrodes 210 can be selected to be a biphasic pole, such that the electrodes alternate between being configured as an anode and a cathode. Also, in embodiments, groups of the electrodes in the first group of electrodes 208 and groups of the electrodes in the second group of electrodes 210 can be selected to be an anode or a cathode or a biphasic pole, such that electric fields can be set up between any two or more groups of the electrodes in the first and second groups of electrodes 208 and 210. In addition, in embodiments, electrodes in the first group of electrodes 208 and the second group of electrodes 210 can be selected to be biphasic pole electrodes, such that during a pulse train including a biphasic pulse train, the selected electrodes alternate between being configured as an anode and a cathode, and the electrodes are not relegated to monophasic delivery where one is always configured as an anode and another is always configured as a cathode.

Further, as described herein, the electrodes are selected to be one of an anode and a cathode, however, it is to be understood without stating it that throughout this disclosure the electrodes can be selected to be biphasic poles, such that they switch or alternate between being configured as anodes and cathodes.

As illustrated in FIG. 2A, one or more of the electrodes in the first group of electrodes 208 are selected to be cathodes and one or more of the electrodes in the second group of electrodes 210 are selected to be anodes. Also, in embodiments, one or more of the electrodes in the first group of electrodes 208 can be selected as a cathode and another one or more of the electrodes in the first group of electrodes 208 can be selected as an anode. In addition, in embodiments, one or more of the electrodes in the second group of electrodes 210 can be selected as a cathode and another one or more of the electrodes in the second group of electrodes 210 can be selected as an anode. Using the characteristics of the catheter 200, the electroporation console 130 can determine models for the various electric fields that can be produced by the catheter 200.

FIG. 2B is a diagram illustrating the catheter 250, in accordance with embodiments of the subject matter of the disclosure. The catheter 250 includes a catheter shaft 252 and catheter splines 254 connected to the catheter shaft 252 at the distal end 256 of the catheter shaft 252. The catheter splines 254 includes a first group of electrodes 258 disposed proximal the maximum circumference of the catheter splines 254 and a second group of electrodes 260 disposed distal the maximum circumference of the catheter splines 254. Each of the electrodes in the first group of electrodes 258 and each of the electrodes in the second group of electrodes 260 is configured to conduct electricity and to be operably connected to the electroporation console 130. In embodiments, one or more of the electrodes in the first group of electrodes 258 and the second group of electrodes 260 includes metal.

Electrodes in the first group of electrodes 258 are spaced apart from electrodes in the second group of electrodes 260. The first group of electrodes 258 includes electrodes 258*a*-258*f* and the second group of electrodes 260 includes electrodes 260*a*-260*f*. Also, electrodes in the first group of electrodes 258, such as electrodes 258*a*-258*f*, are spaced apart from one another and electrodes in the second of electrodes 260, such as electrodes 260*a*-260*f*, are spaced apart from one another.

The spatial relationships and orientation of the electrodes in the first group of electrodes 258 and the spatial relationships and orientation of the electrodes in the second group of electrodes 260 in relation to other electrodes on the same catheter 250 are known or can be determined. In embodiments, the spatial relationships and orientation of the electrodes in the first group of electrodes 258 and the spatial relationships and orientation of the electrodes in the second group of electrodes 260 in relation to other electrodes on the same catheter 250 are variable, where the distal end 262 of the catheter 250 can be extended and retracted which changes the spatial relationships and orientation of the electrodes 258 and 260. In some embodiments, the spatial relationships and orientation of the electrodes in the first group of electrodes 258 and the spatial relationships and orientation of the electrodes in the second group of electrodes 260 on the same catheter 250 is constant, once the catheter 250 is deployed.

As to electric fields, in embodiments, each of the electrodes in the first group of electrodes 258 and each of the electrodes in the second group of electrodes 260 can be selected to be an anode or a cathode, such that electric fields can be set up between any two or more of the electrodes in the first and second groups of electrodes 258 and 260. Also, in embodiments, groups of the electrodes in the first group of electrodes 258 and groups of the electrodes in the second group of electrodes 260 can be selected to be an anode or a cathode, such that electric fields can be set up between any two or more groups of the electrodes in the first and second groups of electrodes 258 and 260.

As illustrated in FIG. 2B, one or more of the electrodes in the first group of electrodes 258 are selected to be cathodes and one or more of the electrodes in the second group of electrodes 260 are selected to be anodes. Also, in embodiments, one or more of the electrodes in the first group of electrodes 258 can be selected as a cathode and another one or more of the electrodes in the first group of electrodes 258 can be selected as an anode. In addition, in embodiments, one or more of the electrodes in the second group of electrodes 260 can be selected as a cathode and another one or more of the electrodes in the second group of electrodes 260 can be selected as an anode. Using the characteristics of the catheter 250 and the surrounding tissue, the electroporation console 130 can determine models for the various electric fields that can be produced by the catheter 250.

Figure 3:
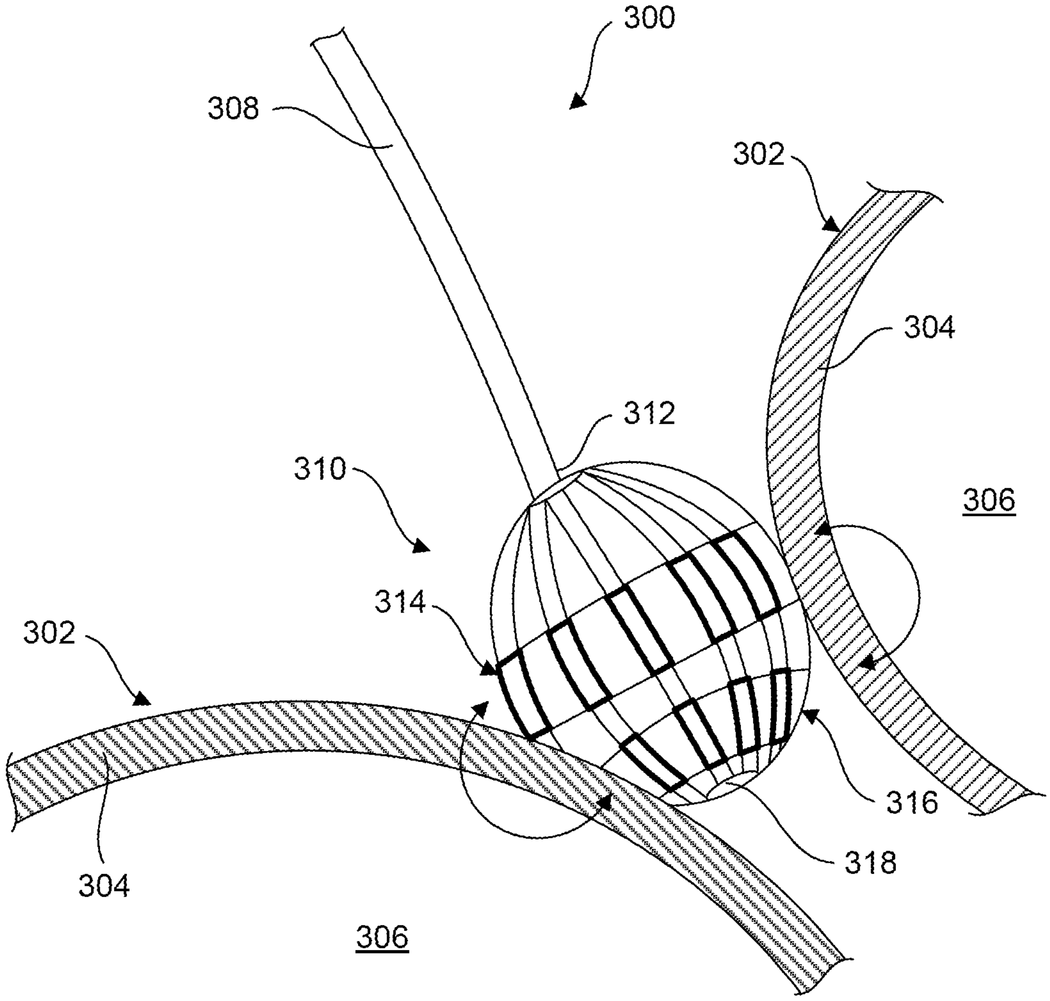
FIG. 3 is a diagram illustrating an electroporation catheter adjacent cardiac tissue in the heart of a patient, in accordance with embodiments of the subject matter of the disclosure.

FIG. 3 is a diagram illustrating an electroporation catheter 300 adjacent cardiac tissue 302 in the heart of a patient, in accordance with embodiments of the subject matter of the disclosure. The cardiac tissue 302 includes endocardium tissue 304 and myocardium tissue 306, where at least some of the endocardium tissue 304 and myocardium tissue 306 may need to be ablated, such as by irreversible electroporation. In embodiments, the cardiac tissue 302 is part of the heart 30 of the patient 20.

The electroporation catheter 300 is suitable for performing irreversible electroporation of the cardiac tissue 302. The electroporation catheter 300 includes a catheter shaft 308 and a basket or splines 310 connected to the catheter shaft 308 at the distal end 312 of the catheter shaft 308. The catheter basket 310 includes a first group of electrodes 314 disposed at the circumference of the catheter basket 310 and a second group of electrodes 316 disposed adjacent the distal end 318 of the catheter basket 310. Each of the electrodes in the first group of electrodes 314 and each of the electrodes in the second group of electrodes 316 is configured to conduct electricity and to be operably connected to the electroporation console 130. In embodiments, one or more of the electrodes in the first group of electrodes 314 and the second group of electrodes 316 includes metal. In embodiments, the electroporation catheter 300 and the electrodes 314 and 316 are like the catheter 200 and the electrodes 208 and 210 previously described herein and, in embodiments, the electroporation catheter 300 and the electrodes 314 and 316 are like the catheter 250 and the electrodes 258 and 260 previously described herein.

The electroporation catheter 300 and the electrodes 314 and 316 are or can be operably connected to the electroporation console 130, where the console 130 is configured to provide electric pulses to the electrodes 314 and 316 to produce electric fields that can ablate cardiac tissue 302 by irreversible electroporation. The dosing of the electric fields provided to the cardiac tissue 302 by the catheter 300, including the electric field strength and the length of time applied to the cardiac tissue 302, determines whether the cardiac tissue 302 is ablated.

For example, an electric field strength of about 400 volts per centimeter (V/cm) is considered large enough to ablate cardiac tissue 302, including myocardium tissue 306, in the heart by irreversible electroporation. While, electric field strengths of 1600 V/cm or more are needed to ablate or kill tissue, such as red blood cells, vascular smooth muscle, endothelium tissue, and nerve tissue, by irreversible electroporation. Also, reversible electroporation of cardiac tissue 302 in the heart can be accomplished with electric field strengths of 200-250 V/cm.

The console 130 is configured to provide the dosing of the electric fields to targeted tissue 302 for ablation or reversible electroporation. The console 130 provides electric pulses of different lengths and magnitudes to the electrodes 314 and 316 on the catheter 300. The electric pulses can be provided in a continuous stream of pulses or in multiple, separate trains of pulses. Pulse parameters of interest include the number of pulses, the duty cycle of the pulses, the spacing of pulse trains, the voltage or magnitude of the pulses including the peak voltages, and the duration of the voltages. To target tissue 302, the console 130 selects two or more electrodes of the electrodes 314 and 316 and provides pulses to the selected electrodes to generate electric fields between the selected electrodes, indicated by arrows in FIG. 3.

To plan ablation by irreversible electroporation, the position of the electroporation catheter 300 in the heart, including the location of the electrodes 314 and 316 in relation to the cardiac tissue 302, needs to be known or determined prior to selecting electrodes of the electrodes 314 and 316 for stimulation. The electrodes on the catheter 300 that are best suited for ablating the cardiac tissue 302 by electroporation, including ablation of targeted surface tissue, such as endocardium tissue 304, and targeted deeper tissue, such as myocardium tissue 306, can be selected for providing the electric fields. Electric pulses are determined for producing the electric fields between the selected electrodes to ablate the tissue 302 by irreversible electroporation. Dosing parameters for the electric fields include electric field strengths and the length of time that the electric field is applied to the tissue 320.

To aid in planning and to improve planning procedures for ablation by electroporation, the console 130 is configured to: determine the location of the electrodes 314 and 316 in the patient in relation to the cardiac tissue 302, after the catheter 300 has been inserted into the patient; model electric fields that can be generated by different combinations of the electrodes 314 and 316 on the catheter 300; determine characteristics of the cardiac tissue 302 near or surrounding the catheter 300 in the patient; determine the surface area and depth of the cardiac tissue 302 that will be or would be affected by an electric field, including determining the strength of the electric field in different portions of the cardiac tissue 302; generate a graphical representation of the electric field of interest; and overlay the graphical representation of the electric field on an anatomical map of the heart. In embodiments, the displayed electric field can be dynamically updated based on which electrodes and vectors are selected to be used for ablation. Also, in embodiments, the displayed electric field can be dynamically updated based on changes in selectable parameters, such as voltage amplitude.

In embodiments, the console 130 receives information from the EAM system 70 to display an anatomical map of the heart and to determine the location of the electrodes 314 and 316 in the patient in relation to the cardiac tissue 302.

In embodiments, the EAM system 70 generates the anatomical map of the heart and utilizes location information for the catheter 300 to generate and display, via the display 92, a detailed three-dimensional geometric anatomical map or representation of the cardiac chambers of the heart and the catheter 300, including the location of the electrodes 314 and 316 in relation to the cardiac tissue 302. In some embodiments, the EAM system 70 generates the anatomical map of the heart and utilizes location information for the catheter 300, along with cardiac electrical activity acquired by, for example, the electroporation catheter 105 or a separate mapping catheter (not shown), to generate and display, via the display 92, a detailed three-dimensional geometric anatomical map of the cardiac chambers, as well as electro-anatomical maps in which cardiac electrical activity of interest is superimposed on the geometric anatomical maps.

In embodiments, the console 130 models the electric fields that can be generated by different combinations of the electrodes 314 and 316 on the catheter 300 based on characteristics of the catheter 300. These characteristics can include the type of catheter, such as a basket catheter that has a constant profile after being opened and a spline catheter that has a variable profile depending on the expansion and retraction of the splines; the form factor of the catheter, such as a balloon catheter, a basket catheter, and a spline catheter; the number of electrodes and the inter-electrode spacing of the electrodes on the catheter; the spatial relationships and orientation of the electrodes on the catheter in relation to other electrodes on the catheter; the type of material that the electrodes are made of; and the shape of the electrodes.

In embodiments, the electric fields that can be generated by electrodes on a spline catheter, such as electrodes 258 and 260 on spline catheter 250, dynamically change depending on the extension and retraction of the catheter 250. Thus, in embodiments, the console 130 models the electric fields of the spline catheter 250 with respect to the extension and retraction of the catheter 250 and the dynamically changing locations of the electrodes 258 and 260. In embodiments, determining the electric fields from different combinations of the electrodes 314 and 316 can be accomplished on a real-time basis, where the location of the catheter 300 and the location of the electrodes 314 and 316 are monitored by a system, such as the EAM system 70.

In embodiments, the console 130 determines characteristics of the cardiac tissue 302 surrounding the catheter 300 by providing electric signals to the electrodes 314 and 316 on the catheter 300 and/or through other electrodes on the catheter 300 or another catheter and measuring the conductance/impedance and/or other properties of the surrounding cardiac tissue 302. In embodiments, the console 130 can receive information about the characteristics of the cardiac tissue 302 near or surrounding the catheter 300 from the EAM system 70, or from other sources. In embodiments, the console 130 can receive information about the characteristics of the cardiac tissue 302 near or surrounding the catheter 300 from other sources, such as from a cardiac computed tomography (CT) scan, a magnetic resonance imaging (MRI) scan, and/or an ultrasound scan. This provides the console 130 with information to show tissue thickness and how much of the tissue thickness will be affected by the electric fields of interest. In embodiments, the console 130 can utilize information from a cardiac CT scan, an MRI, and/or an ultrasound in addition to the EAM data to create the display.

The console 130 determines the surface area and depth of the cardiac tissue 302 that will be or would be affected by an electric field of interest of the different electric fields that can be produced by the different combinations of the electrodes 314 and 316. This includes determining the strength of the electric field in different portions of the cardiac tissue 302 using different pulses. In determining the surface area and depth of the cardiac tissue 302 affected, the console 130 can take into consideration electric pulses of different lengths and magnitudes, where the pulses can be in a continuous stream of pulses or in multiple, separate trains of pulses, or otherwise constituted. Pulse parameters of interest include the number of pulses, the duty cycle of the pulses, the spacing of pulse trains, the voltage or magnitude of the pulses including the peak voltages, and duration of the voltages.

From this information, the console 130 generates a graphical representation of the electric field of interest and overlays the graphical representation of the electric field on the anatomical map of the heart, which is displayed on a display, such as display 92. The electric field of interest to be displayed can be automatically selected by the console 130 based on parameters of the cardiac tissue 302 to be ablated and/or manually selected by a user based on the amount of cardiac tissue 302 to be ablated. In embodiments, the graphical representation and the anatomical map are three-dimensional representations. In embodiments, the console 130 and/or the EAM system 70 can update electrocardiogram information displayed on the anatomical map to guide the user and/or the console 130 in selecting the electric field, including the electric field strength, to be used in electroporation.

In embodiments, the console 130 is configured to graphically depict on the anatomical map where the electric field intersects the cardiac tissue 302. In embodiments, the console 130 is configured to tag the anatomical map with field strength information. In embodiments, the console 130 is configured to mark the graphical depiction of the electric field and the anatomical map with voltage thresholds, such as 200-250 V/cm for reversible electroporation, 400 V/cm for irreversible electroporation, and 1000 V/cm for an extreme or maximum threshold.

FIGS. 4A-4D are diagrams illustrating graphical representations that can be displayed in the overlay of the graphical representation of the electric field on the anatomical map, in accordance with embodiments of the subject matter of the disclosure. In embodiments, the console 130 is configured to display these and other graphical representations in the overlay of the graphical representation of the electric field on the anatomical map on the display 92. In some embodiments, the console 130 is configured to display only a three dimensional surface without thickness in the overlay of the graphical representation of the electric field on the anatomical map.

Each of the FIGS. 4A-4D illustrates the electroporation catheter 300 adjacent the cardiac tissue 302 in the heart of the patient, where the cardiac tissue 302 includes the endocardium tissue 304 and the myocardium tissue 306. The electroporation catheter 300 includes the catheter shaft 308 and the basket 310 connected to the catheter shaft 308. Also, as previously described, the catheter 310 includes the first group of electrodes 314 disposed at the circumference of the catheter basket 310 and the second group of electrodes 316 disposed adjacent the distal end 318 of the catheter basket 310.

Figure 4A:
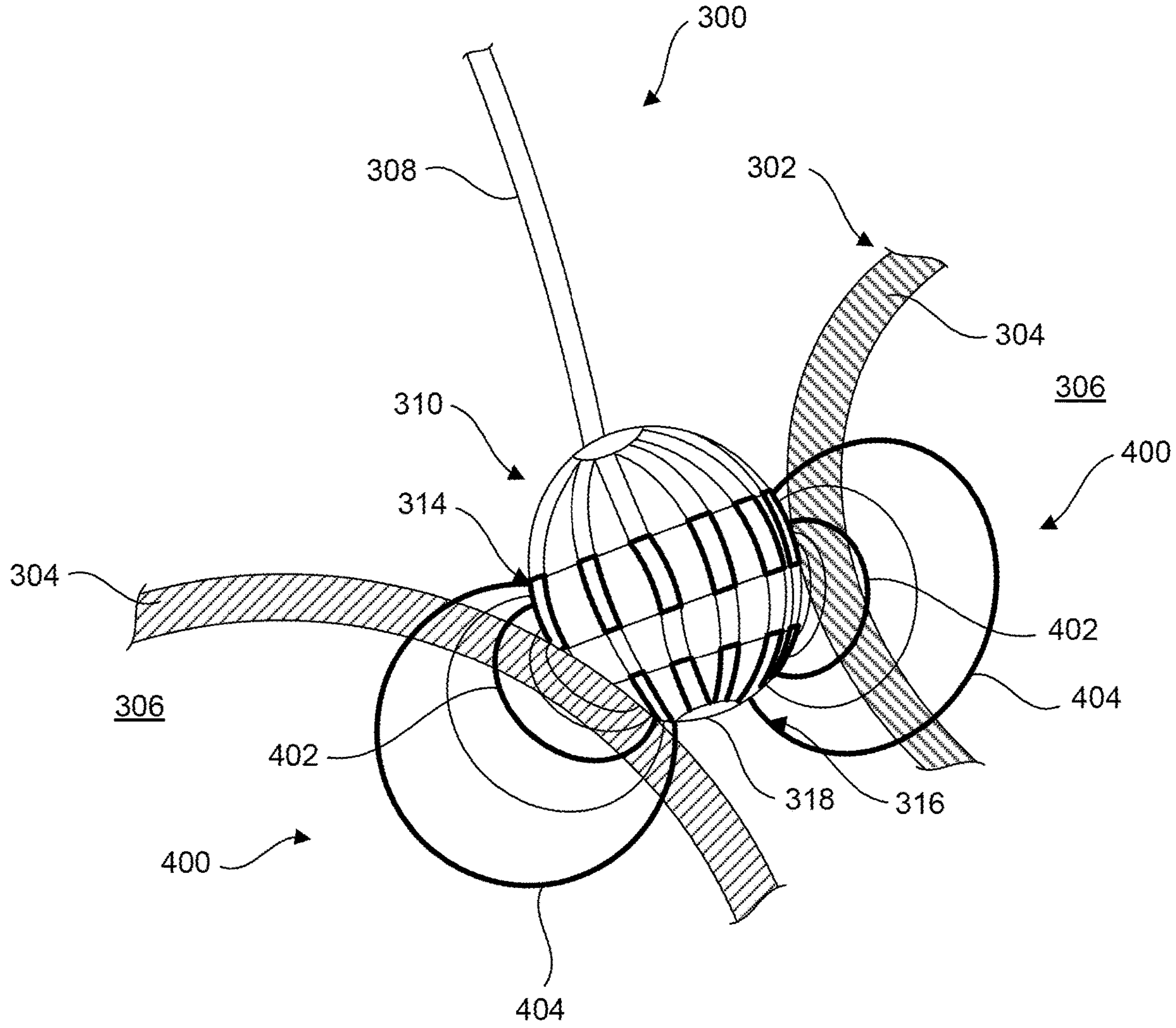
FIG. 4A is a diagram illustrating electric field lines and electric field strength threshold lines in the overlay of the graphical representation of the electric field on the anatomical map, in accordance with embodiments of the subject matter of the disclosure.

FIG. 4A is a diagram illustrating electric field lines 400 and electric field strength threshold lines 402 and 404 in the overlay of the graphical representation of the electric field on the anatomical map, in accordance with embodiments of the subject matter of the disclosure. The electric field lines 400, displayed on the display 92, extend between the first group of electrodes 314 and the second group of electrodes 316. The electric field lines 400 closer to the electrodes 314 and 316 are denser or closer together, indicating a stronger electric field, and the electric field lines 400 further away from the electrodes 314 and 316 are further apart, indicating a weaker electric field. In embodiments, the resolution of the electric field lines 400 can be user selectable. Also, in embodiments, the electric field can be displayed using different colors and minimum/maximum field strength values.

The electric field strength threshold lines 402 and 404 provide the user with an indication of the electric field strength at various distances from the electrodes 314 and 316. Using this information, the user can target cardiac tissue 302 for ablation by irreversible electroporation and/or, in embodiments, the user can target cardiac tissue 302 for reversible electroporation procedures. As illustrated, in embodiments, the electric field strength threshold lines 402 and 404 can be bold lines or wider lines. In embodiments, the electric field strength threshold lines 402 and 404 can be bold lines or wider lines related to the uncertainty in the predicted field strength. In embodiments, the electric field strength threshold lines 402 and 404 can be used to indicate voltage thresholds, such as 200-250 V/cm for reversible electroporation, 400 V/cm for irreversible electroporation, and 1000 V/cm for an extreme or maximum threshold.

In embodiments, the electric field strength threshold line 402 indicates an electric field strength of 400 V/cm, which is considered large enough to ablate cardiac tissue 302, including myocardium tissue 306, by irreversible electroporation. By viewing the electric field strength threshold line 402 on the anatomical map of the heart, and the increased density of the electric field lines 400 closer to the electrodes 314 and 316, the user can determine that cardiac tissue 302 between the electric field threshold line 402 and the electrodes 314 and 316 will or can be ablated by irreversible electroporation. Also, in embodiments, the electric field strength threshold line 404 indicates an electric field strength of 200 V/cm, which provides the user with an indication of a limit for reversible electroporation of cardiac tissue 302.

In some embodiments, since electric field strengths of 1600 V/cm or more will ablate or kill tissue, such as red blood cells, vascular smooth muscle, endothelium tissue, and nerve tissue, by irreversible electroporation, a maximum or extreme electric filed strength threshold line is provided on the display 92 to alert the user to excessive electric field strengths.

Figure 4B:
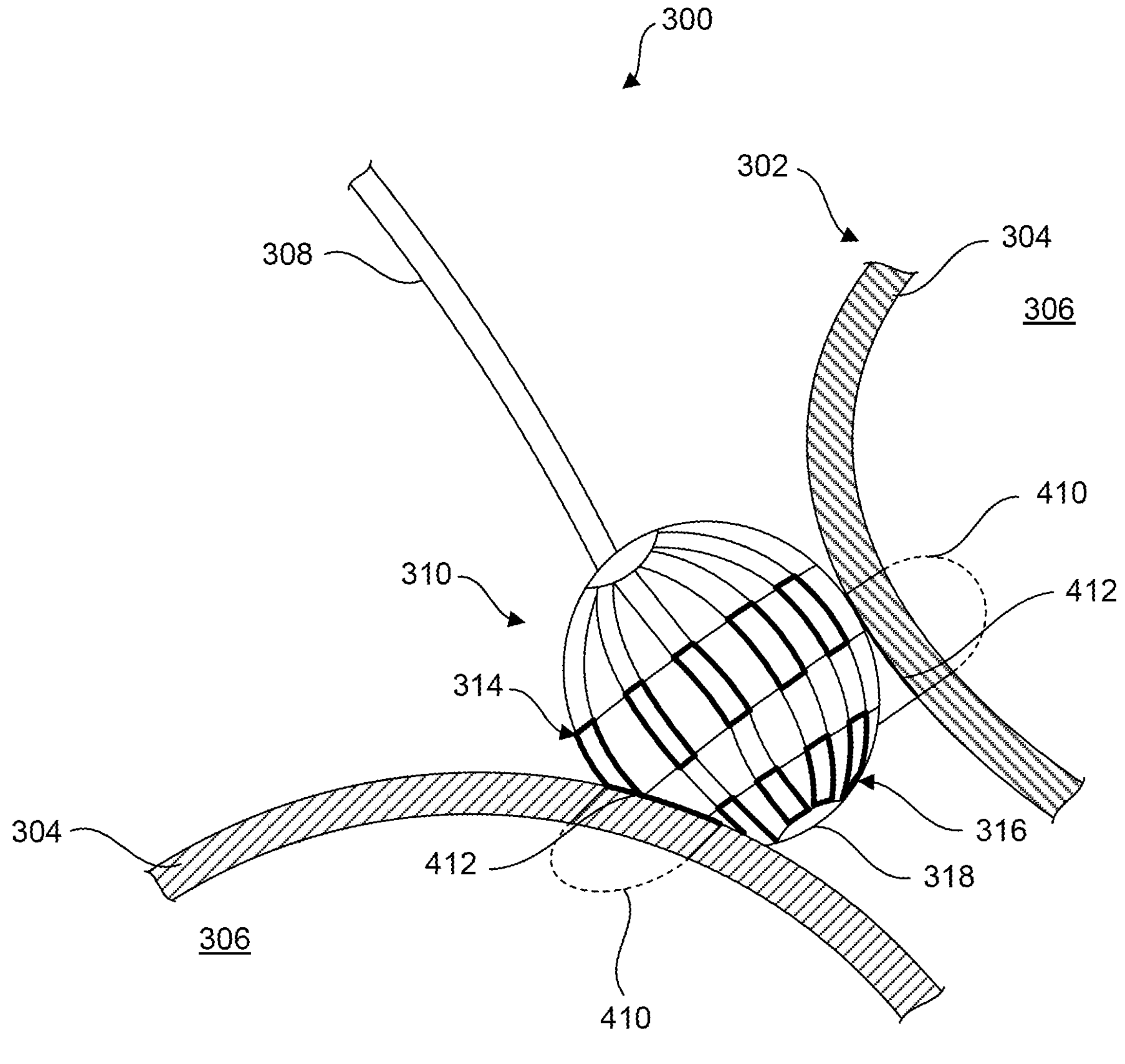
FIG. 4B is a diagram illustrating the intersection of the electric field at a given electric field strength, such as 400 V/cm, with the cardiac tissue in the overlay of the graphical representation of the electric field on the anatomical map, in accordance with embodiments of the subject matter of the disclosure.

FIG. 4B is a diagram illustrating the intersection 410 of the electric field at a given electric field strength, such as 400 V/cm, with the cardiac tissue 302 in the overlay of the graphical representation of the electric field on the anatomical map, in accordance with embodiments of the subject matter of the disclosure. The intersection 410 of the electric field with the cardiac tissue 302 on the anatomical map provides an indication of the size of the lesion that will or can be created in the cardiac tissue 302. Also, in embodiments, the bolder lines 412 in the graphical representation mark or indicate the surface area of the endocardium tissue 304 that will be affected by the electric field.

In embodiments, the intersection 410 can be combined with three dimensional images, such as CT, MRI, or ultrasound images, of the anatomy of the heart to provide a three dimensional image of the lesion depth at the critical or given electric field strength. Of course, the lesion size, including the area and depth of the lesion, changes based on different pulse parameters of the electric pulses applied to the electrodes 314 and 316 of the catheter 300.

Figure 4C:
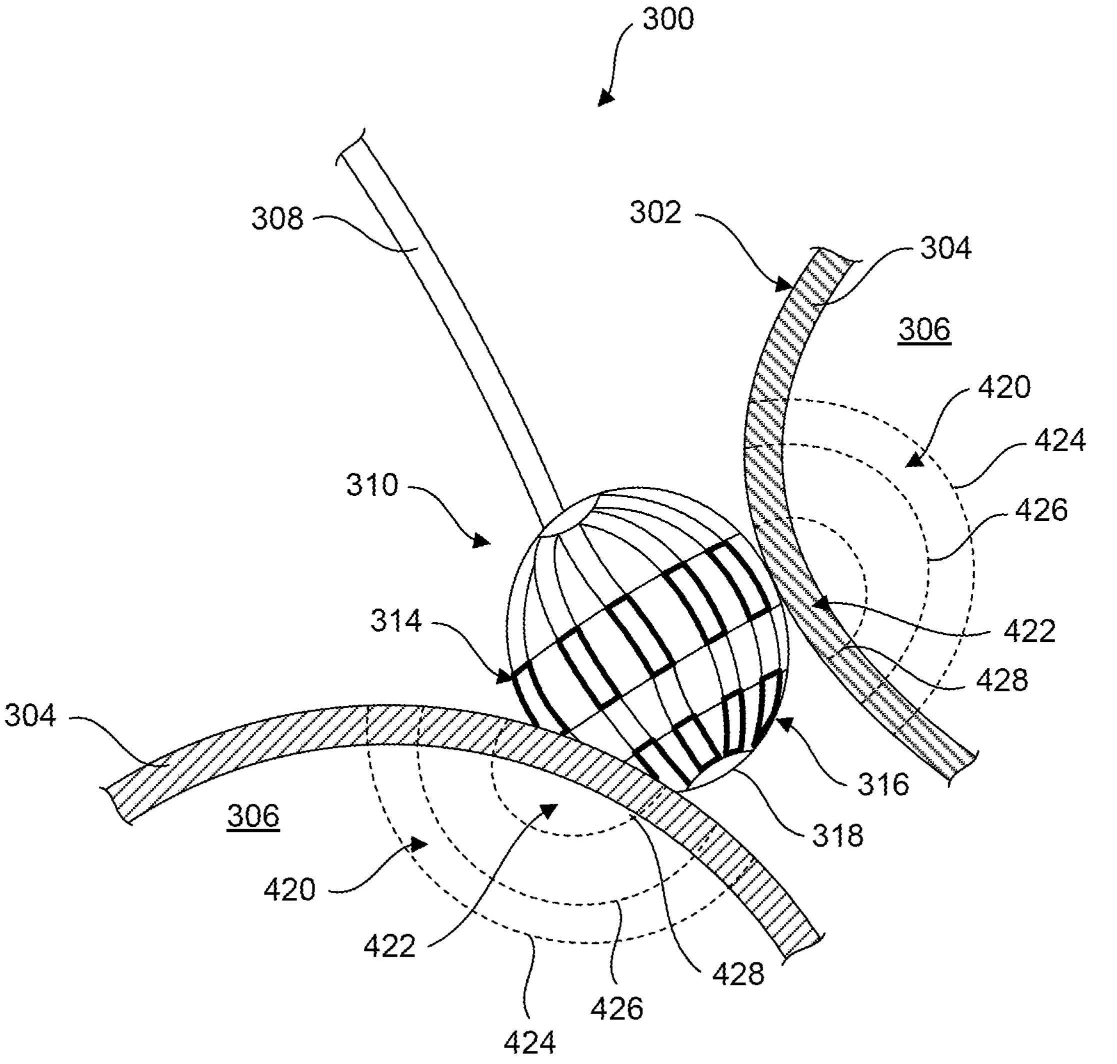
FIG. 4C is a diagram illustrating a predicted zone of reversible electroporation and a predicted zone of irreversible electroporation in the overlay of the graphical representation of the electric field on the anatomical map, in accordance with embodiments of the subject matter of the disclosure.

FIG. 4C is a diagram illustrating a predicted zone of reversible electroporation 420 and a predicted zone of irreversible electroporation 422 in the overlay of the graphical representation of the electric field on the anatomical map, in accordance with embodiments of the subject matter of the disclosure. In embodiments, the predicted zones 420 and 422 are determined based on models of the electric fields that will be or could be generated using selected electrodes of the electrodes 314 and 316 and based on simulations of various electric pulses being applied to the selected electrodes. Where, the area and depth of the predicted zones 420 and 422 change depending on different pulse parameters of the electric pulses applied to the electrodes 314 and 316 of the catheter 300.

Electric field strength threshold lines 424 and 426 define the predicted zone of reversible electroporation 420. In embodiments, the electric field strength threshold line 424 indicates 200 V/cm and the electric field strength threshold line 426 indicates 250 V/cm.

Electric field strength threshold line 428 and the endocardium tissue 304 boundary define the predicted zone of irreversible electroporation 422. In embodiments, the electric field strength threshold line 428 indicates an electric field strength of 400 V/cm.

Figure 4D:
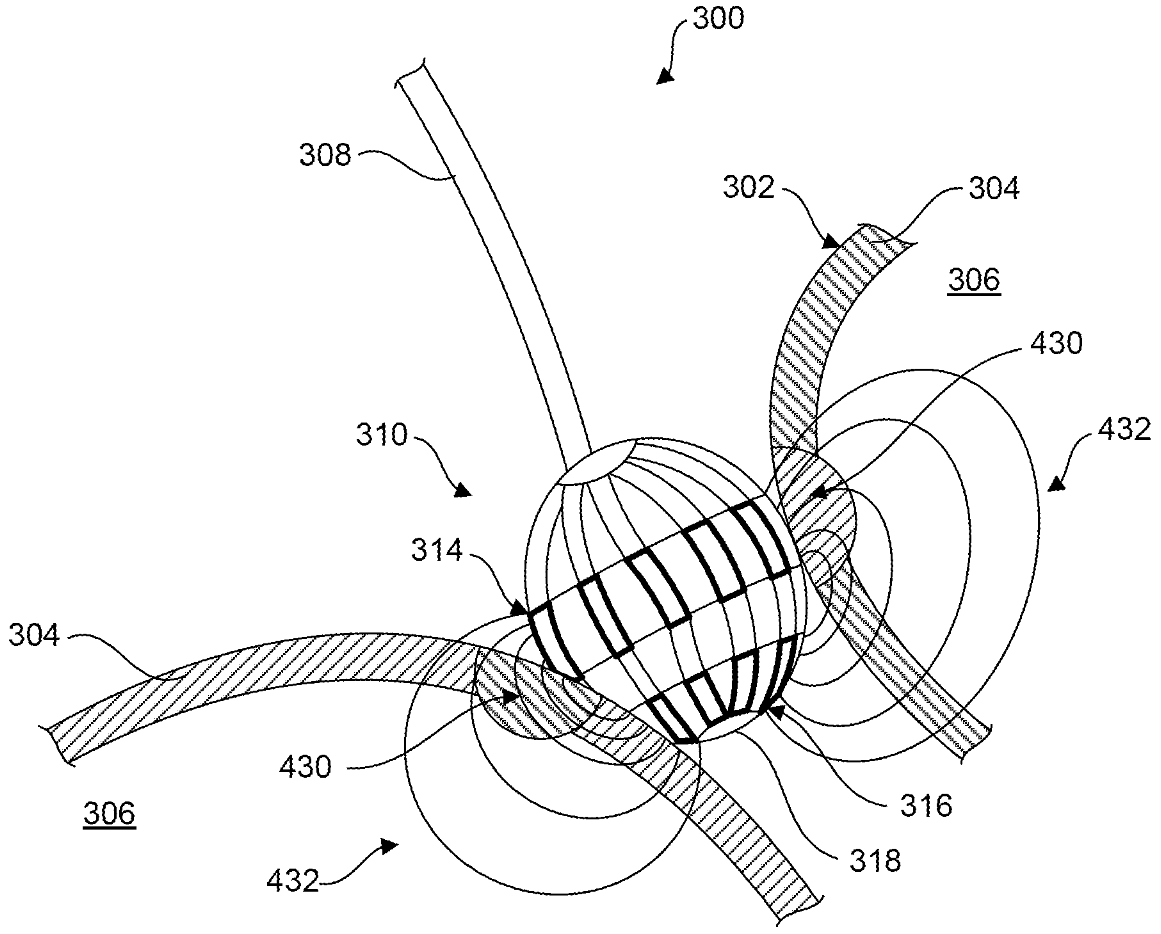
FIG. 4D is a diagram illustrating lesions previously created in the cardiac tissue intersecting with electric field lines in the overlay of the graphical representation of the electric field on the anatomical map, in accordance with embodiments of the subject matter of the disclosure.

FIG. 4D is a diagram illustrating lesions 430 previously created in the cardiac tissue 302 intersecting with electric field lines 432 in the overlay of the graphical representation of the electric field on the anatomical map, in accordance with embodiments of the subject matter of the disclosure.

In some embodiments, local complex tissue impedance values of the cardiac tissue 302 surrounding the catheter 300 may be added to the anatomical map, either during the initial mapping process and/or post ablation. These local complex tissue impedance values can be used to indicate the underlying tissue substrate, including viable and diseased myocardium, fibrosis, vein tissue, inflammation, and previously ablated cardiac tissue 302. Which can be useful in predicting the reversible and irreversible electroporation zones as the local complex tissue impedance affects the local electric field.

In another aspect of the disclosure, set-points can be created to provide a constant critical electric field size and/or depth relative to the catheter 300 and the anatomical structures of the surrounding cardiac tissue 302. In embodiments, the console 130 is configured to dynamically change or suggest manual changes to the voltage amplitude and/or other pulse parameters in response to dynamically measured impedance changes in the surrounding cardiac tissue 302 and/or changes in the shape of the catheter 300 and the locations of the electrodes 314 and 316 to provide a constant critical electric field size, depth, and/or location.

Figure 5:
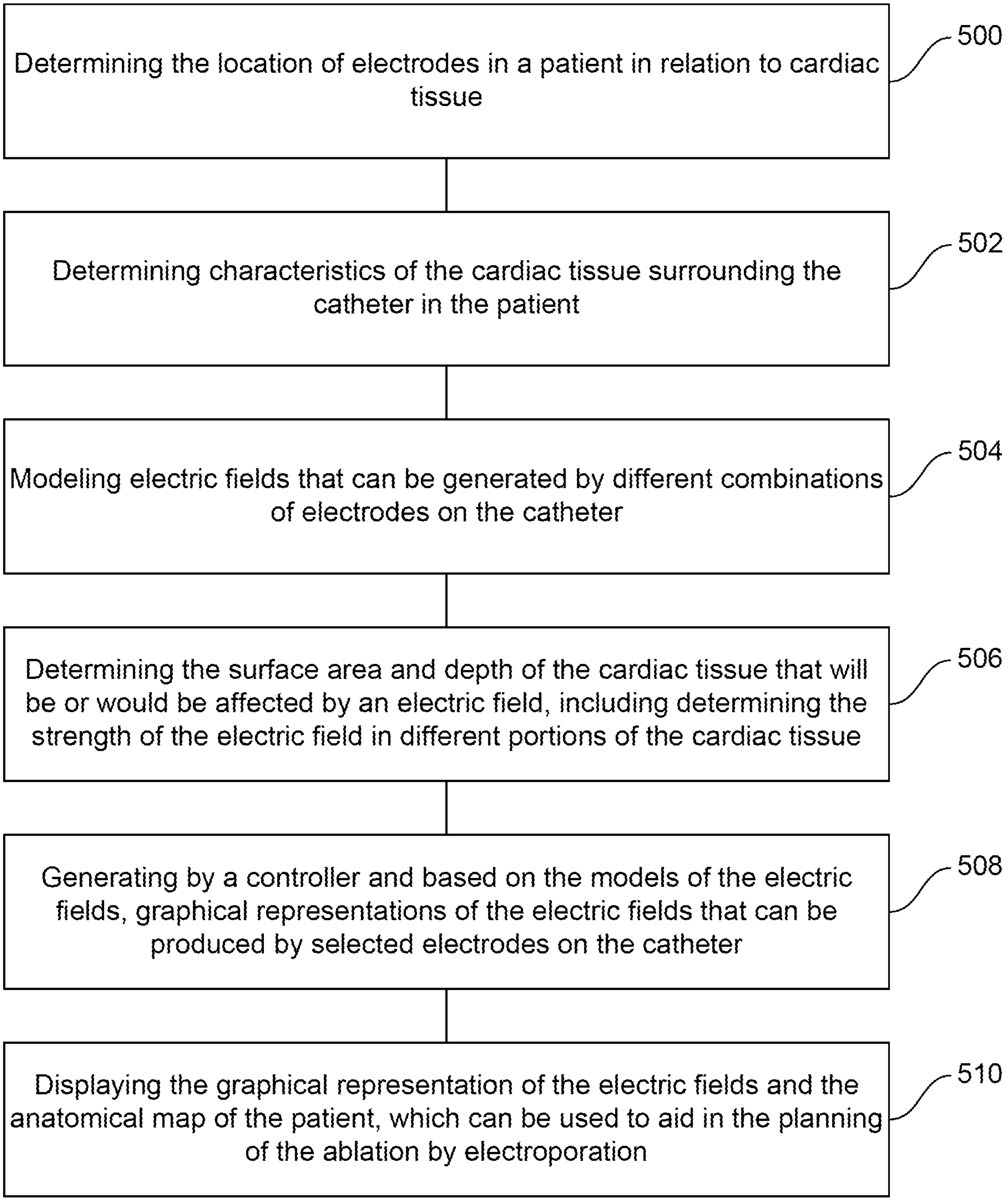
FIG. 5 is a method of planning ablation by irreversible electroporation, in accordance with embodiments of the subject matter of the disclosure.

FIG. 5 is a method of planning ablation by irreversible electroporation, in accordance with embodiments of the subject matter of the disclosure. The method is described in relation to catheter 300, however, any suitable electroporation catheter can be used in the method. Also, in embodiments, the console 130 and/or the EAM 70 are configured or can be configured to provide the functions of the various steps of the method.

At 500, the method includes determining the location of the electrodes 314 and 316 in the patient in relation to the cardiac tissue 302, after the catheter 300 has been inserted into the patient and, at 502, the method includes determining characteristics of the cardiac tissue 302 near or surrounding the catheter 300 in the patient.

At 504, the method includes modeling electric fields that can be generated by different combinations of the electrodes 314 and 316 on the catheter 300. Also, in some embodiments, the method includes selecting electrodes of the electrodes 314 and 316, which appear to be best suited for ablating the targeted cardiac tissue 302 by electroporation, including ablation of targeted surface tissue and deeper tissue. In embodiments, this includes providing user inputs like voltage amplitude.

At 506, the method includes determining the surface area and depth of the cardiac tissue 302 that will be or would be affected by an electric field, including determining the strength of the electric field in different portions of the cardiac tissue 302. In embodiments, this includes determining electric pulses for producing the electric fields between the selected electrodes to ablate the tissue 302 by irreversible electroporation. Also, in embodiments, this includes determining dosing parameters for the electric fields, such as electric field strengths and the length of time that the electric field is to be applied to the cardiac tissue 302.

At 508, the method includes generating by a controller, such as console 130, and based on the models of the electric fields, graphical representations of the electric fields that can be produced using the selected electrodes on the catheter 300. In embodiments, the method includes generating the graphical representations of the electric fields based on characteristics of the catheter 300, the position or location of the catheter 300 in the patient, and characteristics of the cardiac tissue 302 surrounding the catheter 300 in the patient.

At 510, the method includes displaying, on a display such as display 92, the graphical representations of the electric fields and the anatomical map of the patient, which can be used to aid in the planning of the ablation by electroporation, prior to delivering energy. In embodiments, this includes overlaying the graphical representation of the electric field of interest on the anatomical map of the heart. In embodiments, displaying the graphical representations includes displaying electric field strength that is based on electric pulse parameters of electric pulses to be provided to the selected electrodes of the electrodes 314 and 316.

In embodiments, the graphical representation can include displaying one or more of the following: displaying at least one of electric field lines in the graphical representations of the electric field on the anatomical map, electric field strength threshold lines in the graphical representations of the electric field on the anatomical map, markings where electric field strength threshold lines intersect surrounding tissue, displaying a predicted zone of reversible electroporation, displaying a predicted zone of irreversible electroporation, displaying markings where the electric fields intersect previously created lesions, and displaying a predicted lesion on the anatomical map.

Also, in embodiments, the method includes dynamically changing, by the controller, the graphical representations of the electric fields based on one or more of changes in position of the catheter relative to surrounding tissue, changes in the catheter, changes in pulse parameters to be provided to the electrodes of the catheter; and changes in measured impedance values of the surrounding tissue.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. A system for ablation of a cardiac tissue by electroporation, comprising:

a catheter having a plurality of electrodes;

a display; and a controller configured to:

determine, for a position of the catheter, a location of each of the plurality of electrodes in relation to an anatomical map of the cardiac tissue;

determine a plurality of combinations of anodes and cathodes of the plurality of electrodes suited for electroporation of the cardiac tissue from the plurality of electrodes at the position;

determine a characteristic of the cardiac tissue including complex impedance prior to any instance of ablation of the cardiac tissue;

generate graphical representations of electric fields that can be produced using the determined plurality of combinations of anodes and cathodes of the plurality of electrodes and the determined characteristic of the cardiac tissue including the complex impedance prior to delivering ablation energy, the graphical representations including each of an area and a depth of a predicted lesion; and overlay, on the display, the graphical representations of the electric fields and the anatomical map to aid in planning the ablation by electroporation, prior to delivering the ablation energy, the overlay based on the location of each of the plurality of the electrodes;

wherein the graphical representation of the electric fields includes each of a predicted zone of reversible electroporation and a predicted zone of irreversible electroporation.

2. The system of claim 1, wherein the graphical representations of the electric fields are based on characteristics of the catheter.

3. The system of claim 1, wherein the controller is configured to display strengths of the electric fields based on electric pulse parameters of electric pulses to be provided to the plurality of electrodes of the catheter.

4. The system of claim 1, wherein the controller is configured to include at least one of electric field lines in the graphical representations of the electric fields on the anatomical map or electric field strength threshold lines in the graphical representations of the electric fields on the anatomical map.

5. The system of claim 1, wherein the controller is configured to include in the graphical representations of the electric fields at least one of a reversible electric field strength threshold line in a range of 200-250 volts per centimeter, a critical electric field strength threshold line of 400 volts per centimeter for irreversible electroporation, and an extreme electric field strength threshold line of 1000 volts per centimeter.

6. The system of claim 1, wherein the controller is configured to include markings where electric field strength threshold lines of the electric fields intersect with surrounding cardiac tissue in the graphical representations of the electric fields.

7. The system of claim 1, wherein the controller is configured to include markings where the electric fields intersect previously created lesions in the graphical representations of the electric fields.

8. The system of claim 1, wherein the controller is configured to include a predicted lesion in the graphical representations of the electric fields.

9. A system for ablation by electroporation, comprising:

a catheter having a plurality of electrodes; and a controller configured to:

determine a characteristic of cardiac tissue including complex impedance prior to ablation of the cardiac tissue;

generate models of electric fields based on characteristics of the catheter for a plurality of combinations of anodes and cathodes of the plurality of electrodes suited for electroporation of surrounding cardiac tissue from the plurality of electrodes at a position of the catheter and the determined characteristic of the cardiac tissue including the complex impedance prior to any instance of delivering ablation energy after mapping of the cardiac tissue;

generate graphical representations of the electric fields using the models of the electric fields;

display the graphical representations of the electric fields on an anatomical map of a patient to aid in planning the ablation by electroporation, prior to delivering the ablation energy; and dynamically change the graphical representations of the electric fields in real time based on changes in position of the catheter relative to the surrounding cardiac tissue, changes in pulse parameters to be provided to the plurality of electrodes of the catheter and changes in measured complex impedance of the surrounding cardiac tissue prior to delivering the ablation energy.

10. The system of claim 9, wherein the controller is configured to provide one or more of suggested changes to the pulse parameters and automatic dynamic changes to the pulse parameters in response to at least one of the measured complex impedance of the surrounding cardiac tissue and changes in the catheter to maintain a critical electric field strength of the electric fields at a location.

11. The system of claim 9, comprising a plurality of sensing electrodes on the catheter, wherein the controller is configured to display real-time information from the plurality of sensing electrodes and the graphical representations of the electric fields on the anatomical map of the patient to aid in optimizing the catheter position, prior to delivering the ablation energy.

12. A method of planning ablation by electroporation of cardiac tissue, comprising;

determining, at a position, by a controller a plurality of combinations of anodes and cathodes of a plurality of electrodes suited for electroporation of the cardiac tissue;

determining a local complex impedance value prior to ablation of the cardiac tissue;

generating, by the controller and based on models of electric fields, graphical representations of the electric fields that can be produced using the determined plurality of combinations of anodes and cathodes of the plurality of electrodes on a catheter prior to any instance of delivering ablation energy;

displaying, on a display, the graphical representations of the electric fields overlaying an anatomical map of a patient to aid in the planning of the ablation by electroporation, prior to delivering the ablation energy;

overlaying the local complex impedance value on the anatomical map; and dynamically changing the graphical representations of the electric fields based on changes in position of the catheter relative to surrounding cardiac tissue, changes in pulse parameters to be provided to the plurality of electrodes of the catheter and changes in the local complex impedance value of the surrounding cardiac tissue prior to delivering the ablation energy.

13. The method of claim 12, wherein generating the graphical representations of the electric fields includes generating the graphical representations of the electric fields based on characteristics of the catheter and the position of the catheter in the patient relative to the surrounding cardiac tissue.

14. The method of claim 12, comprising displaying strengths of the electric fields based on the pulse parameters of electric pulses to be provided to the plurality of electrodes of the catheter.

15. The method of claim 12, comprising displaying at least one of electric field lines in the graphical representations of the electric fields on the anatomical map or electric field strength threshold lines in the graphical representations of the electric fields on the anatomical map.

16. The method of claim 12, the graphical representations of the electric fields comprising one or more of displaying markings where electric field strength threshold lines of the electric fields intersect the surrounding cardiac tissue, displaying a predicted zone of reversible electroporation, displaying a predicted zone of irreversible electroporation, displaying markings where the electric fields intersect previously created lesions, or displaying a predicted lesion on the anatomical map.

* * * * *